United States Patent
Cefali et al.

(10) Patent No.: US 6,818,229 B1
(45) Date of Patent: Nov. 16, 2004

(54) INTERMEDIATE RELEASE NICOTINIC ACID COMPOSITIONS FOR TREATING HYPERLIPIDEMIA

(75) Inventors: Eugenio A. Cefali, Fort Lauderdale, FL (US); David J. Bova, Boca Raton, FL (US)

(73) Assignee: KOS Pharmaceuticals, Inc., Miami, FL (US)

( * ) Notice: Subject to any disclaimer, the term of this patent is extended or adjusted under 35 U.S.C. 154(b) by 148 days.

(21) Appl. No.: 08/962,027

(22) Filed: Oct. 31, 1997

Related U.S. Application Data

(63) Continuation-in-part of application No. 08/814,974, filed on Mar. 6, 1997, now Pat. No. 6,129,930, which is a continuation-in-part of application No. 08/368,378, filed on Jan. 14, 1995, now Pat. No. 6,080,428, which is a continuation-in-part of application No. 08/124,292, filed on Sep. 20, 1993, now abandoned.

(51) Int. Cl.[7] .............................................. A61K 9/20

(52) U.S. Cl. ........................ 424/464; 424/400; 424/465

(58) Field of Search ................................ 424/464, 400, 424/465, 489; 514/255

(56) References Cited

U.S. PATENT DOCUMENTS

| | | |
|---|---|---|
| 2,510,164 A | 6/1950 | Woodward et al. |
| 2,540,979 A | 2/1951 | Clymer et al. |
| 2,749,274 A | 6/1956 | Buckwalter |
| 2,798,837 A | 7/1957 | Sahyun |
| 2,798,838 A | 7/1957 | Robinson |
| 2,805,977 A | 9/1957 | Robinson et al. |
| 2,851,453 A | 9/1958 | Kennon et al. |
| 2,857,313 A | 10/1958 | Cooper et al. |
| 2,887,436 A | 5/1959 | Klioze et al. |
| 2,957,804 A | 10/1960 | Schuyler |
| 3,062,720 A | 11/1962 | Costello |
| 3,065,143 A | 11/1962 | Christenson et al. |
| 3,108,046 A | 10/1963 | Harbit |

(List continued on next page.)

FOREIGN PATENT DOCUMENTS

| | | |
|---|---|---|
| CA | 603 690 | 8/1960 |
| EP | 0 109 320 | 5/1984 |
| EP | 0 126 453 | 11/1984 |
| EP | 0 349 235 A2 | 1/1990 |

(List continued on next page.)

OTHER PUBLICATIONS

Dialog File 326: Trademarkscan(r)—US FED: Accession No. 73/838497.
McCarthy on Patents, Sec. 19.110.
199 U.S.P.O. 824 [*Endo Laboratories, Inc. v. Fredericks*, Aug. 18, 1978].
Keenan, et al., A Clinical Trial of Oat Dran and Niacin in the Treatment of Hyperlipidemia, Jour. Fam. Prac., 34:3, 313–317 (1992).
Knopp, et al., "Contrasting Effects of Unmodified and Time–Release forms of Niacin on Lipoproteins in Hyperlipidemic Subjects: Clues to Mechanism of Action of Niacin", Metabolism, 34:7, 642–650(1985).
Letter to Applicant from U.S. Department of Health and Human Services dated Jul. 28, 1997.

(List continued on next page.)

*Primary Examiner*—Thurman K. Page
*Assistant Examiner*—Robert M. Joynes
(74) *Attorney, Agent, or Firm*—Karen J. Messick

(57) ABSTRACT

Intermediate release nicotinic acid formulations having unique biopharmaceutical characteristics, such as Cmax, Tmax and AUC, which are suitable for oral administration once per day during the evening or at night for treating hyperlipidemia without causing drug-induced hepatotoxicity to such a level that requires the therapy to be discontinued, are disclosed. The intermediate nicotinic acid formulations can be administered as tablets in dosage strengths of, for example, 375 mg, 500 mg, 750 mg and 1000 mg.

28 Claims, 5 Drawing Sheets

U.S. PATENT DOCUMENTS

Figure 1:
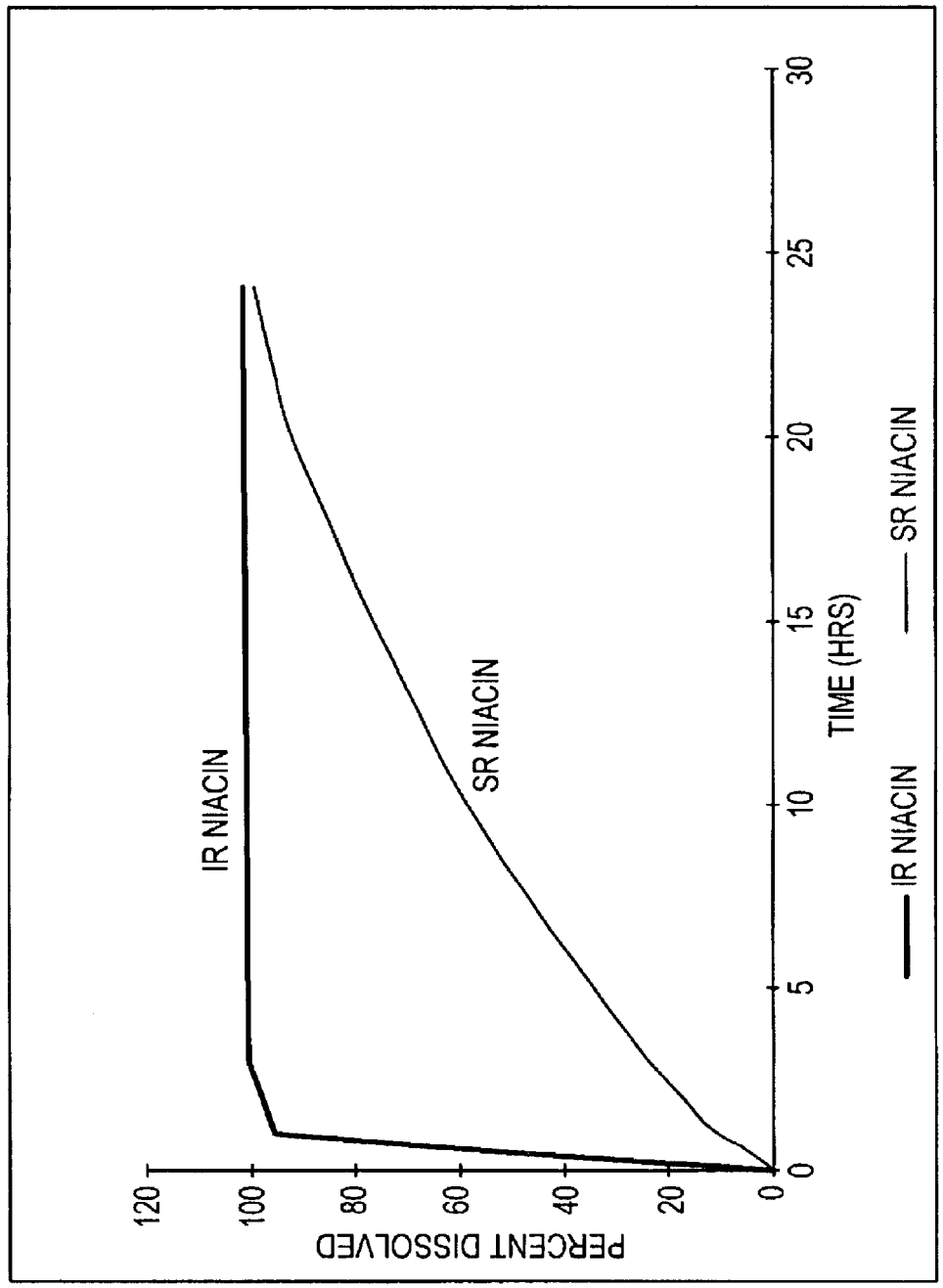

| | | |
|---|---|---|
| 3,116,204 A | 12/1963 | Siegel et al. |
| 3,134,719 A | 5/1964 | Sheth et al. |
| 3,143,469 A | 8/1964 | Debay et al. |
| 3,147,187 A | 9/1964 | Playfair |
| 3,193,461 A | 7/1965 | Eisen |
| 3,210,413 A | 10/1965 | Blank et al. |
| 3,272,832 A | 9/1966 | Nakano et al. |
| 3,336,200 A | 8/1967 | Krause et al. |
| 3,424,842 A | 1/1969 | Nürnberg |
| 3,495,011 A | 2/1970 | Fossel |
| 3,590,117 A | 6/1971 | Christenson et al. |
| 3,626,071 A | 12/1971 | Kariya et al. |
| 3,629,393 A | 12/1971 | Nakamota et al. |
| 3,629,453 A | 12/1971 | Waring |
| 3,634,584 A | 1/1972 | Poole |
| 3,639,636 A | 2/1972 | Barnhart |
| 3,709,991 A | 1/1973 | Miller |
| 3,721,735 A | 3/1973 | Thiffault |
| 3,773,920 A | 11/1973 | Nakamoto et al. |
| 3,795,691 A | 3/1974 | Douglas et al. |
| 3,806,601 A | 4/1974 | Mikite et al. |
| 3,849,554 A | 11/1974 | Winitz |
| 3,859,437 A | 1/1975 | Weigand |
| 3,862,332 A | 1/1975 | Barnhart et al. |
| 3,864,416 A | 2/1975 | Albright et al. |
| 3,870,790 A | 3/1975 | Lowey et al. |
| 3,923,972 A | 12/1975 | Fields et al. |
| 3,924,001 A | 12/1975 | Albright et al. |
| 3,930,017 A | 12/1975 | Kummer et al. |
| 3,951,821 A | 4/1976 | Davidson |
| 3,957,976 A | 5/1976 | Sugimoto |
| 3,959,492 A | 5/1976 | Coulston et al. |
| 3,965,255 A | 6/1976 | Bloch et al. |
| 3,977,404 A | 8/1976 | Theeuwes |
| 3,987,160 A | 10/1976 | Broughton et al. |
| 3,992,536 A | 11/1976 | Kleemann |
| 4,002,641 A | 1/1977 | Möller et al. |
| 4,008,719 A | 2/1977 | Theeuwes et al. |
| 4,011,339 A | 3/1977 | Galantay et al. |
| 4,014,334 A | 3/1977 | Theeuwes et al. |
| 4,014,987 A | 3/1977 | Heller et al. |
| 4,034,087 A | 7/1977 | Voorhees |
| 4,034,758 A | 7/1977 | Theeuwes |
| 4,058,122 A | 11/1977 | Theeuwes et al. |
| 4,067,876 A | 1/1978 | Ferruti et al. |
| 4,077,407 A | 3/1978 | Theeuwes et al. |
| RE29,652 E | 5/1978 | Fields et al. |
| 4,102,806 A | 7/1978 | Kondo et al. |
| 4,115,550 A | 9/1978 | Fields et al. |
| 4,116,241 A | 9/1978 | Theeuwes et al. |
| 4,117,111 A | 9/1978 | Fields et al. |
| 4,126,672 A | 11/1978 | Sheth et al. |
| 4,140,755 A | 2/1979 | Sheth et al. |
| 4,160,020 A | 7/1979 | Ayer et al. |
| 4,160,452 A | 7/1979 | Theeuwes |
| 4,166,902 A | 9/1979 | Ferruti |
| 4,167,558 A | 9/1979 | Sheth et al. |
| 4,169,944 A | 10/1979 | Scallen et al. |
| 4,178,387 A | 12/1979 | Diamond et al. |
| 4,180,064 A | 12/1979 | Heller et al. |
| 4,182,902 A | 1/1980 | Thiele et al. |
| 4,203,439 A | 5/1980 | Theeuwes |
| 4,205,085 A | 5/1980 | Shepherd |
| 4,211,783 A | 7/1980 | Shepherd |
| 4,226,849 A | 10/1980 | Schor |
| 4,230,878 A | 10/1980 | Shepherd |
| 4,237,118 A | 12/1980 | Howard |
| 4,248,857 A | 2/1981 | DeNeale et al. |
| 4,251,519 A | 2/1981 | Robbins et al. |
| 4,255,449 A | 3/1981 | Cavazza |
| 4,256,108 A | 3/1981 | Theeuwes |
| 4,259,314 A | 3/1981 | Lowey |
| 4,261,970 A | 4/1981 | Ogawa et al. |
| 4,268,524 A | 5/1981 | Cavazza |
| 4,272,548 A | 6/1981 | Gatzen et al. |
| 4,279,898 A | 7/1981 | Engel et al. |
| 4,282,233 A | 8/1981 | Vilani |
| 4,283,382 A | 8/1981 | Frank et al. |
| 4,285,951 A | 8/1981 | Hoefle |
| 4,291,030 A | 9/1981 | Mulinos |
| 4,305,959 A | 12/1981 | Shepherd |
| 4,308,251 A | 12/1981 | Dunn et al. |
| 4,309,404 A | 1/1982 | DeNeale et al. |
| 4,310,545 A | 1/1982 | Shepherd |
| 4,318,914 A | 3/1982 | Shepherd |
| 4,326,525 A | 4/1982 | Swanson et al. |
| 4,348,399 A | 9/1982 | Shepherd |
| 4,353,887 A | 10/1982 | Hess et al. |
| 4,357,469 A | 11/1982 | Schor |
| 4,361,546 A | 11/1982 | Stricker et al. |
| 4,362,711 A | 12/1982 | Cerami |
| 4,367,217 A | 1/1983 | Gruber et al. |
| 4,369,172 A | 1/1983 | Schor et al. |
| 4,375,468 A | 3/1983 | Dunn |
| 4,382,143 A | 5/1983 | Shepherd |
| 4,389,393 A | 6/1983 | Schor et al. |
| 4,428,951 A | 1/1984 | Hata et al. |
| 4,432,966 A | 2/1984 | Zeitoun et al. |
| 4,440,940 A | 4/1984 | Shepherd |
| 4,452,775 A | 6/1984 | Kent |
| 4,454,108 A | 6/1984 | Iida et al. |
| 4,455,298 A | 6/1984 | McFarlane et al. |
| 4,457,907 A | 7/1984 | Porter et al. |
| 4,461,759 A | 7/1984 | Dunn |
| 4,465,660 A | 8/1984 | David et al. |
| 4,472,436 A | 9/1984 | Hooper |
| 4,478,819 A | 10/1984 | Hercelin et al. |
| 4,485,105 A | 11/1984 | Shepherd |
| 4,505,890 A | 3/1985 | Jain et al. |
| 4,522,804 A | 6/1985 | Dunn |
| 4,525,345 A | 6/1985 | Dunn et al. |
| 4,539,198 A | 9/1985 | Powell et al. |
| 4,540,566 A | 9/1985 | Davis et al. |
| 4,547,359 A | 10/1985 | Zierenberg et al. |
| 4,556,678 A | 12/1985 | Hsiao et al. |
| 4,568,547 A | 2/1986 | Herschler |
| 4,571,333 A | 2/1986 | Hsiao |
| 4,576,604 A | 3/1986 | Guittard et al. |
| 4,603,142 A | 7/1986 | Burger et al. |
| 4,605,666 A | 8/1986 | Schmidt et al. |
| 4,610,870 A | 9/1986 | Jain et al. |
| 4,624,950 A | 11/1986 | Sasaki et al. |
| 4,657,757 A | 4/1987 | Hanna et al. |
| 4,673,405 A | 6/1987 | Guittard et al. |
| 4,678,516 A | 7/1987 | Alderman et al. |
| 4,680,323 A | 7/1987 | Lowey |
| 4,684,516 A | 8/1987 | Bhutani |
| 4,690,824 A | 9/1987 | Powell et al. |
| 4,692,337 A | 9/1987 | Ukigaya et al. |
| 4,695,467 A | 9/1987 | Uemura et al. |
| 4,695,591 A | 9/1987 | Hanna et al. |
| 4,695,910 A | 9/1987 | Maruyama et al. |
| 4,696,762 A | 9/1987 | Sander et al. |
| 4,704,285 A | 11/1987 | Alderman |
| 4,708,834 A | 11/1987 | Cohen et al. |
| 4,710,519 A | 12/1987 | Finnan et al. |
| 4,713,245 A | 12/1987 | Ando et al. |
| RE32,581 E | 1/1988 | Scherm et al. |
| 4,729,895 A | 3/1988 | Makino et al. |
| 4,734,285 A | 3/1988 | Alderman |
| 4,744,907 A | 5/1988 | Klimchak et al. |

| | | | | | | |
|---|---|---|---|---|---|---|
| 4,747,881 A | 5/1988 | Shaw et al. | | 4,996,058 A | 2/1991 | Sinnreich |
| 4,749,575 A | 6/1988 | Rotman | | 4,997,658 A | 3/1991 | Alberts et al. |
| 4,752,479 A | 6/1988 | Briggs et al. | | 4,999,380 A | 3/1991 | Berger et al. |
| 4,753,801 A | 6/1988 | Oren et al. | | 5,002,774 A | 3/1991 | Agrawala et al. |
| 4,755,544 A | 7/1988 | Makino et al. | | 5,009,895 A | 4/1991 | Lui |
| 4,756,911 A | 7/1988 | Drost et al. | | 5,010,105 A | 4/1991 | Lee |
| 4,758,581 A | 7/1988 | Scherm et al. | | 5,011,947 A | 4/1991 | Catt et al. |
| 4,759,923 A | 7/1988 | Buntin et al. | | 5,015,479 A | 5/1991 | Mulligan et al. |
| 4,764,374 A | 8/1988 | Grimberg | | 5,023,245 A | 6/1991 | Kuhrts |
| 4,775,483 A | 10/1988 | Mookerjea et al. | | 5,025,012 A | 6/1991 | Miura et al. |
| 4,775,535 A | 10/1988 | Lowey | | 5,030,653 A | 7/1991 | Trivedi |
| 4,777,042 A | 10/1988 | Toda et al. | | 5,032,406 A | 7/1991 | Dansereau et al. |
| 4,784,858 A | 11/1988 | Ventouras | | 5,034,528 A * | 7/1991 | Izydore et al. ............... 514/223 |
| 4,789,549 A | 12/1988 | Khan et al. | | 5,039,341 A | 8/1991 | Meyer et al. |
| 4,792,452 A | 12/1988 | Howard et al. | | 5,047,248 A | 9/1991 | Calanchi et al. |
| 4,792,554 A | 12/1988 | Elben et al. | | 5,049,696 A | 9/1991 | Lee et al. |
| 4,794,115 A | 12/1988 | Takahashi et al. | | 5,096,714 A | 3/1992 | Kuhrts |
| 4,795,327 A | 1/1989 | Gaylord et al. | | 5,100,675 A | 3/1992 | Cho et al. |
| 4,795,642 A | 1/1989 | Cohen et al. | | 5,110,817 A | 5/1992 | Beyer, Jr. |
| 4,795,644 A | 1/1989 | Zentner | | 5,110,940 A | 5/1992 | Sit et al. |
| 4,803,079 A | 2/1989 | Hsiao et al. | | 5,116,610 A | 5/1992 | Broaddus |
| 4,803,081 A | 2/1989 | Falk et al. | | 5,126,145 A | 6/1992 | Evenstad et al. |
| 4,812,316 A | 3/1989 | Rossi et al. | | 5,128,142 A | 7/1992 | Mulligan et al. |
| 4,814,183 A | 3/1989 | Zentner | | 5,130,333 A | 7/1992 | Pan et al. |
| 4,814,354 A | 3/1989 | Ghere-Sellassie et al. | | 5,132,116 A | 7/1992 | Sournac et al. |
| 4,824,672 A | 4/1989 | Day et al. | | 5,133,974 A | 7/1992 | Paradissis et al. |
| 4,824,677 A | 4/1989 | Shah et al. | | 5,145,678 A | 9/1992 | Gakic et al. |
| 4,828,836 A | 5/1989 | Elger et al. | | 5,167,964 A | 12/1992 | Muhammad et al. |
| 4,830,859 A | 5/1989 | Finnan | | 5,169,638 A | 12/1992 | Dennis et al. |
| 4,834,965 A | 5/1989 | Martani et al. | | 5,169,639 A | 12/1992 | Baichwal et al. |
| 4,834,985 A | 5/1989 | Elger et al. | | 5,169,640 A | 12/1992 | France et al. |
| 4,837,032 A | 6/1989 | Ortega | | 5,171,570 A | 12/1992 | Takemori et al. |
| 4,839,177 A | 6/1989 | Colombo et al. | | 5,178,854 A | 1/1993 | Asami et al. |
| 4,842,863 A | 6/1989 | Nishimura et al. | | 5,182,298 A | 1/1993 | Helms et al. |
| 4,844,907 A | 7/1989 | Elger et al. | | 5,188,839 A | 2/1993 | Pearmain |
| 4,849,229 A | 7/1989 | Gaylord et al. | | 5,190,940 A | 3/1993 | Commons et al. |
| 4,851,232 A | 7/1989 | Urquhart et al. | | 5,190,970 A | 3/1993 | Pan et al. |
| 4,851,233 A | 7/1989 | Khan et al. | | 5,196,440 A | 3/1993 | Bertolini et al. |
| 4,855,143 A | 8/1989 | Lowey | | 5,211,958 A | 5/1993 | Akkerboom et al. |
| 4,857,336 A | 8/1989 | Khanna et al. | | 5,213,808 A | 5/1993 | Bar-Shalom et al. |
| 4,866,058 A * | 9/1989 | Izydore et al. ............... 514/241 | | 5,256,689 A | 10/1993 | Chiang |
| 4,871,548 A | 10/1989 | Edgren et al. | | 5,258,401 A | 11/1993 | Berger et al. |
| 4,882,167 A | 11/1989 | Jang | | 5,260,305 A * | 11/1993 | Dennick ..................... 514/255 |
| 4,886,669 A | 12/1989 | Ventouras | | 5,262,165 A | 11/1993 | Govil et al. |
| 4,888,178 A | 12/1989 | Rotini et al. | | 5,262,435 A | 11/1993 | Joshua et al. |
| 4,892,741 A | 1/1990 | Ohm et al. | | 5,264,226 A | 11/1993 | Graille et al. |
| 4,911,917 A | 3/1990 | Kuhrts | | 5,268,181 A | 12/1993 | O'Neill et al. |
| 4,915,952 A | 4/1990 | Ayer et al. | | 5,278,067 A | 1/1994 | Dawson et al. |
| 4,920,115 A | 4/1990 | Nestler et al. | | 5,286,736 A | 2/1994 | Soyka et al. |
| 4,920,123 A | 4/1990 | Beyer, Jr. | | 5,314,697 A | 5/1994 | Kwan et al. |
| 4,925,905 A | 5/1990 | Boeckh et al. | | 6,406,715 B1 * | 6/2002 | Cefali ........................ 424/468 |
| 4,935,246 A | 6/1990 | Ahrens | | | | |
| 4,940,588 A | 7/1990 | Sparks et al. | | | | |
| 4,942,040 A | 7/1990 | Ragnarsson et al. | | | | |
| 4,946,870 A | 8/1990 | Partain, III. et al. | | | | |
| 4,946,963 A | 8/1990 | Izydore et al. | | | | |
| 4,950,689 A | 8/1990 | Yang et al. | | | | |
| 4,952,402 A | 8/1990 | Sparks et al. | | | | |
| 4,959,478 A | 9/1990 | Möller et al. | | | | |
| 4,963,367 A | 10/1990 | Ecanow | | | | |
| 4,965,252 A | 10/1990 | Kuhrts | | | | |
| 4,966,768 A | 10/1990 | Michelucci et al. | | | | |
| 4,968,508 A | 11/1990 | Oren et al. | | | | |
| 4,970,081 A | 11/1990 | Frisbee | | | | |
| 4,973,468 A | 11/1990 | Chiang et al. | | | | |
| 4,973,469 A | 11/1990 | Mulligan et al. | | | | |
| 4,983,398 A | 1/1991 | Gaylord et al. | | | | |
| 4,990,535 A | 2/1991 | Cho et al. | | | | |
| 4,992,278 A | 2/1991 | Khanna | | | | |
| 4,994,267 A | 2/1991 | Sablotsky | | | | |
| 4,994,276 A | 2/1991 | Baichwal et al. | | | | |

FOREIGN PATENT DOCUMENTS

| | | |
|---|---|---|
| EP | 0 577 504 A1 | 1/1994 |
| FR | 1 302 362 | 7/1962 |
| GB | 2 141 338 | 12/1984 |
| GB | 2 154 874 | 9/1985 |
| JP | 40-2053 | 2/1965 |
| JP | 46-18151 | 5/1971 |
| JP | 55-049312 | 9/1980 |
| WO | WO84/00104 | 1/1984 |

OTHER PUBLICATIONS

English language translation of Abstract of Japanese Patent No. JP63310827 A 881219 Derwent DW8905 (1988).

English language translation of Abstract of Japanese Patent No. JP5221854 A 930831 Derwent DW9339 A61K9/22 (1993).

Slow Niacin Advertisement, *Am. Druggist*, 141–142 (1988).
Regulatory Letter to Upsher–Smith Laboratories (Jun. 6, 1988).
"Issues in Cholesterol Management: Reappraisal of Niacin," (Ed. Hunninghake), Upsher–Smith Laboratories, 1–7 (1990).
"Report of the National Cholesterol Education Program Expert Panel on Detection, Evaluation, and Treatment of High Blood Cholesterol in Adults," The Expert Panel, *Arch. Intern. Med.*, 148:36–69, (1988).
Handbook of Nonprescription Drugs, Nutritional Supplements, 9th Edition, American Pharmaceutical Association, 470–471 (1990).
"Clofibrate and Niacin in Coronary Heart Disease," The Coronary Project Research Group, *JAMA*, 231(4):360–381 (1975).
Abumrad, N.A., et al., "Studies on Serum lipids, Insulin, and Glucagon and on Muscle Triglyceride in Rats Adapted to High–fat and High–carbohydrate Diets," *J. Lipid Res.*, 19:423–432 (1978).
Alderman, J.D., et al., "Major Favorable Changes in cholesterol and HDL in Coronary Patients Using a Modified Niacin Regimen," *Clin. Res.*, Abstract 1883, III–471 (1985).
Alderman, J.D., et al., "Effect of a Modified, Well–Tolerated Niacin Regimen on Serum Total Cholesterol, High Density Lipoprotein Cholesterol and the Cholesterol to High Density Lipoprotein Ratio," *Am. J. Cardiol.*, 64(12):725–729 (1989).
Altschul, R., et al., "Influence of Oxygen Inhalation on Cholesterol Metabolism," Letters to the Editors, *Arch. Biochem. Biophys.*, 51:308–309 (1954).
Altschul, R., et al., "Influence of Nicotinic Acid on Serum Cholesterol in Man," Letters to the Editors, *Arch. Biochem. Biophys,.* 54:558–559 (1955).
Altschul, R., et al., "Niacin In Vascular Disorders And Hyperlipemia," Charles C. Thomas Publ., Springfield, IL, 42–47; 116–133 (1964).
Andreotti, F., et al., "Major Circadian Fluctuations in Fibrinolytic Factors and Possible Relevance Time on Onset of Myocardial Infarction, Sudden Cardiac Death and Stroke," *Am. J. Cardiol.*, 62:635–637 (1988).
Angleton, P., et al., "Diurnal Variation of Tissue–Type Plasminogen Activator and Its Rapid Inhibitor (PAI–1)," *Circulation*, 79:101–106 (1989).
Barter, P.J., et al., "Diurnal Fluctuations in Triglyceride, Free Fatty Acids, and Insulin During Sucrose Consumption and Insulin Infusion in Man," *J. Clin. Invest.*, 50:583–591 (1971).
Berge, K.G., et al., "Hypercholesteremia and Nicotinic Acid: A Long–Term Study," *Am. J. Med.*, 31:24–35 (1961).
Blankenhorn, D.H., et al., "Beneficial Effects of Combined Colestipol–Niacin Therapy on Coronary Atherosclerosis and Coronary Venous Bypass Grafts," *JAMA*, 257(23):3233–3240 (1987).
Blum, C.B., et al., "Current Therapy for Hypercholesterolemia," *JAMA*, 261(24):3582–3587 (1989).
Brown, G., et al., "Regression of Coronary Artery Disease as a Result of Intensive Lipid–Lowering Therapy in Men with High Levels of Apoliprotein B," *N. Engl. J. Med.*, 323(19):1289–1298 (1990).
Buri, P., et al., "Formulation des comprimés à libération prolongée II. Matrices hydrophiles," ("Formulation of sustained–release tablets. II. Hydrophilic matrices") *Pharm. ACTA Helv.*, 33(7–8):189–197 (1980) (with English–translation of the abstract).

Canner, P.L., et al., "Fifteen Year Mortality in Coronary Drug Project Patients: Long–Term Benefit With Niacin," *J. Am. Coll. Cardiol.*, 8(6):1245–1255 (1986).
Carlson, L.A., "Inhibition of the Mobilization of Free Fatty Acid from Adipose Tissue," *Ann. NY Acad. Sci.*, III(471):119–142.
Carlson, L.A., et al., "The Effect of Nicotinic Acid on the Plasma Free Fatty Acids: Demonstration of a Metabolic Type of Symphathicolysis," *Acta Med. Scand.*, 172:641–645 (1962).
Carlson, L.A., "Studies on the Effect of Nicotinic Acid on Catecholamine Stimulated Lipolysis in Adipose Tissue in Vitro," *Acta Med. Scand.*, 173:719–722 (1963).
Carlson, L.A., et al., "Acute Effects of Nicotinic Acid in the Rat. I. Plasma and Liver Lipids and Blood Glucose," *Acta Med. Scand.*, 179:453–461 (1966).
Carlson, L.A., "Determination of Free Nicotinic Acid in Blood Plasma," *Clin. Chim. Acta*, 13:349–351 (1966).
Carlson, L.A., et al., "Consequences of Inhibition of Normal and Excessive Lipid Mobilization. Studies with Nicotonic Acid," *Prog. Biochem. Pharmacol.*, 3:151–166 (1967).
Carlson, L.A., et al., "Effect of a Single Dose of Nicotinic Acid on Plasma Lipids in Patients with Hyperlipoproteinemia," *Acta Med. Scand.*, 183:457–465 (1968).
Carlson, L.A., et al., "Plasma Lipids and Urinary Excretion of Catecholamines in Man during Experimentally Induced Emotional Stress, and Their Modification by Nicotinic Acid," *J. Clin. Invest.*, 47:1795–1805 (1968).
Carlson, L.A., et al., "Pronounced Lowering of Serum Levels of Lipoprotein Lp(a) in Hyperlipidaemic Subjects Treated with Nicotinic Acid," *J. Int. Med.*, 226(5):271–276 (1989).
Cayen, M.N., "Metabolic Disposition of Antihyperlipidemic Agents in Man and Laboratory Animals," *Drug Metab. Rev.*, 11(2):291–323 (1980).
Cayen, M.N., et al., "Effect of AY–25,712 on Fatty Acid Metabolism in Rats," *Arteriosclerosis* 45(3):281–290 (1982).
Chandler, W.L., et al., "Insulin, Cortisol and Catecholamines Do Not Regulate Circadian Variations in Fibrinolytic Activity," *Thrombosis Res.*, 58(1):1–12 (1990).
Chowhan, Z.T., et al., "Hardness Increase Induced by Partial Moisture Loss in Compressed Tablets and Its Effect on In Vitro Dissolution," *J. Pharm. Sci.*, 67(10):1385–1389 (1978).
Chowhan, Z.T., "Role of Binders in Moisture–Induced Hardness Increase in Compressed Tablets and Its Effect on In Vitro Disintegration and Dissolution," *J. Pharm. Sci.*, 69(1):1–3 (1980).
Chowhan, Z.T., et al., "Compression Properties of Granulations Made with Binders Containing Different Moisture Contents," *J. Pharm. Sci.*, 70(1):1134–1139 (1981).
Christensen, N.A., et al., "Nicotinic Acid Treatment of Hypercholesteremia, Comparison of Plain and Sustained–Action Preparation and Report of Two Cases of Jaundice" *JAMA*, 177(8):76–80 (1961).
Cooper, K.H., "The Wisdom and Risk of Drug and Vitamin Therapy," *Dr. Kenneth H. Cooper's Preventive Medicine Program, Controlling Cholesterol*, 244–252, Bantam Books (1988).
Criscuoli, M., et al., "Glunicate (LG 13979) Protects the Arterial Wall from Cholesterol–Induced Atherosclerotic Changes in the Rabbit Without Affecting Plasma Lipids," *Atherosclerosis*, 53(1):59–68 (1984).

Dalton, T.A., et al., "Hepatotoxicity Associated with Sustained–Release Niacin," *Am. J. Med.*, 93:102–104 (1992).

Davis, S.S., et al., *Modern Concepts in Nitrate Delivery Systems*, 30–37, (Eds. A.A.J. Goldbert, D.G. Parsons), 1983 Royal Soc. of Med. Int'l. Congress & Symp. Series No. 54, published jointly by Academic Press Inc. (London) Ltd. and Royal Society of Medicine.

Dow, "Formulating for Controlled Release with METHOCEL Premium Cellulose Ethers," Dow Chemical Company publications, 1–33 (1995).

Dow, "METHOCEL as a Binding Agent for Tablet production by Wet Granulation," Dow Chemical Company publication, 1–15 (1985).

Dow, "Viscosity: Molecular Weight–Viscosity Relationship," Handbook on METHOCEL* Cellulose Ether Products, Dow Chemical Company publication (1974).

Dow, "Technical Information: Methods of Formulating Controlled Release Products Outside the Forest Lab Patent US 4,389,393 Claims".

Dow, "Formulating Sustained Release Pharmaceutical Products with METHOCEL," Dow Chemical Company publication.

Dow, product designation changes for METHOCEL cellulose ethers, Dow Chemical Company publication (1985) (CZ).

Dow, product designation changes for METHOCEL cellulose ethers, Dow Chemical Company publication (DG) (1960).

Ekström–Jodal, B., et al., "Influence of Nicotinic Acid and Pentaerythrioltetranicotinate (Perycit®, Bofors) on the Cardiac Output in Man," *Pharmacologia Clinica*, 2:86–89 (1970).

Etchason, J.A., et al., "Niacin–Induced Hepatitis: A Potential Side Effect with Low–Dose Time–Release Niacin," *Mayo Clin. Proc.*, 66:23–28 (1991).

Figge, H.L., et al., "Comparison of Excretion of Nicotinuric Acid After Ingestion of Two Controlled Release Nicotinic Acid Preparations in Man," *J. Clin. Pharmacol.*, 28:1135–1140 (1988).

Figge, H.L., et al., "Nicotinic Acid: A Review of Its Clinical Use in the Treatment of Lipid Disorders," *Pharmacotherapy*, 8(5):287–294 (1988).

Fleischman, A.I., et al., Low Dose Sustained Release Nicotinic Acid As An Effective Hypo Lipidemic Agent In Man, *Fed. Proc,*. 34(1):248 (1975).

Gray, D.R., et al. "Efficacy and Safety of Controlled–release Niacin in Dyslipoproteinemic Veterans," *Ann. Intern. Med.* 121:252–258 (1994).

Gudsoorkar, V.R., et al., "Influence of Binders on Some Physical Parameters of Lactose and Sulfadimidine Tablets," *Indian Drugs & Pharmaceuticals Industry*, 3–4 (Jul.–Aug. 1980).

Hamsten, A., et al., "Increased Plasma Levels of a Rapid Inhibitor of Tissue Plasminogen Acitvator in Young Suvivors of Myocardial Infarction," *N. Engl. J. Med.*, 313(25):1557–1563 (1985).

Henkin, Y., et al., "Rechallenge With Crystalline Niacin After Drug–Induced Hepatitis From Sustained–Release Niacin," *JAMA*, 264(2):241–243 (1990).

Henkin, Y., et al., "Niacin Revisited: Clinical Observations on an Inportant but Underutilized Drug," *Am. J. Med.*, 91:239–246 (1991).

Hodis, H.N., "Acute Hepatic Failure Associated With the Use of Low–Dose Sustained–Release Niacin," Letter to the Editors, *JAMA*, 264(2):181 (1990).

Huber, H.E., et al., "Utilization of Hydrophilic Gums for the Control of Drug Release from Tablet Formulations I. Disintegration and Dissolution Behavior," *J. Pharm. Sci.*, 55(9):974–976 (1966).

Ibrahim, S.A., et al., "Release Characteristics of Oxyphenbutazone from Different Suppository Bases," *Pharmazie*, 35(8):567 (1980).

Jacobson, T.A., et al., "Combination Therapy with Fluvastatin and Niacin in Hypercholesterolemia: A Preliminary Report on Safety," *Am. J. Cardiol.*, 73:25D–29D (1994).

Kane, J.P., et al., "Normalization of Low–Density–Lipoprotein Levels in Heterozygous Familial Hypercholesterolemia with a Combined Drug Regimen," *N. Engl. J. Med.,*, 304(5):251–258 (1981).

Kassem, A.A., et al., "Enhancement of Release Rate of Spironolactone from Its Tablets by the Formation of Solid Dispersions with Water–Soluble Polymers," *Jami et Al–Qahira, Faculty of Pharmacy, Cairo University, Bulletin, Cairo*, 19(1):275–306 (1980).

Keenan, J. M., et al., "Niacin Revisited: A Randomized, Controlled Trial of Wax–Matrix Sustained–Release Niacin in Hypercholesterolemia," *JAMA Spec. J. Abst.*, 266(16):2209 (1991).

Keenan, J.M., et al., "Niacin Revisited A Randomized, Controlled Trial of Wax–Matrix Sustained–Release Niacin in Hypercholesterolemia," *Arch. Intern. Med.*, 151:1424–1432 (1991).

Keenan, J.M., et al., "Treatment of Hypercholesterolemia: Comparison of Younger versus Older Patients Using Wax–Matrix Sustained–Release Niacin," *J. Am. Geriat. Soc.*, 40:12–18 (1992).

King, R.E., "Tablets, Capsules, and Pills," *Remington's Pharm. Sci.*, 1576–1587 (1975).

Kirschstein, W., et al., "Impaired Fibrinolytic Capacity and Tissue Plasminogen Activator Release in Patents with Restenosis after Percutaneous Transluminal Coronary Angioplasty (PTCA)," *Thromb. Haemost.*, 62(2):772–775 (1989).

Knopp, R.H., et al., "Contrasting Effects of Unmodified and Time–Release Forms of Niacin on Lipoproteins in Hyperlipidemic Subjects: Clues to Mechanism of Action of Niacin," *Metabolism*, 34(7):642–650 (1985).

Korsmeyer, R.W., et al., "Mechanisms of Potassium Chloride Release from Compressed, Hydrophilic, Polymeric Matrices: Effect of Entrapped Air," *J. Pharm. Sci.*, 72(10):1189–1191 (1983).

Kowalski, R.E., The 8–Week Cholesterol Cure, Harper & Row, Publishers, 95–115 (1989).

Kruse, W., et al., "Nocturnal Inhibition of Lipolysis in Man by Nicotinic Acid and Derivatives," *Eur. J. Clin. Pharmacol.*, 16:11–15 (1979).

Krycer, I., et al., "An Evaluation of Tablet Binding Agents Part I. Solution Binders," *Powder Technol.*, 34:39–51 (1983).

Laguna, O., et al., "Enrobage. III. Influence de quelques produits filmogènes et plastifiants sur la dissolution de comprimés à base de chlorure de sodium." ("Coatings. III. Influence of various filmogenic products and plasticizers on the dissolution of tablets with a sodium chloride base") *Ann. Pharma. Franc.*, 33(5):235–242 (1975). This document relates to the dissolution properties of sodium chloride–based tablets coated with filmogenic products and plasticizers.

Lapidus, H., et al., "Some Factors Affecting The Release of a Water–Soluble Drug from a Compressed Hydrophilic Matrix," *J. Pharm. Sci.*, 55(8):840–843 (1966).

Lapidus, H., "Drug Release from Compressed Hydrophilic Matrices," *University Microfilms International*, Thesis, Rutgers University, 1–117 (1967).

Lapidus, H., *Chemistry, Abstract*, (order No. 67–14,728) 2363–B2364–B (1967).

Lapidus, H., et al., "Drug Release From Compressed Hydrophilic Matrices," *J. Pharm. Sci.*, 57(8):1292–1301 (1968).

Leiner, P., Chain Drug Review Publication, 12 (Jun. 6, 1988).

Luria, M.H., "Effect of Low–Dose Niacin on High–Density Lipoprotein Cholesterol and Total Cholesterol/High–Density Lipoprotein Cholesterol Ratio," *Arch. Intern. Med.*, 148:2493–2495 (1988).

Mahl, M., et al., "A Long Term Study of the Effect of Nicotinic Acid Medication on Hyperclodesteremia," *Am. J. Med. Sci.*, 64:673–677 (1963).

Malkowska, S., et al., "Effect of Re–Compression on the Properties of Tablets Prepared by Moist Granulation," *Drug Dev. Indust. Pharmacy*, Marcel Dekker, Inc., 9(3):349–361 (1983).

Manninen, M., et al., "Lipid Alterations and Decline in the Incidence of Coronary Heart Disease in the Helsinki Heart Study," *JAMA*, 260(5):641–651 (1988).

Merck & Co. Inc., The Merck Index, Tenth Ed., 809, 520, 351, 466 (1983).

Miettinen, T.A., "Diurnal Variation of LDL and HDL Cholesterol," *Ann. Clin. Res.*, 12:295–298 (1980).

Miettinen, T.A., "Cholesterol Precursors and Their Diurnal Rhythm in Lipoproteins of Patients with Jejuno–Ileal Bypass and Ileal Dysfunction," *Metabolism*, 34(5):425–430 (May 1985).

Miettinen, T.A., "Diurnal Variation of Cholesterol Precursors Squalene and Methyl Sterols in Human Plasma Lipoproteins," *J. Lipid Res.*, 23:466–473 (1982).

Miettinen, T.A., "Detection of Changes in Human Cholesterol Metabolism," *Ann. Clin. Res.*, 2:300–320 (1970).

Miller, O.N., et al., "Investigation of the Mechanism of Action of Nicotinic Acid on Serum Lipid Levels in Man," *Am. J. Clin. Nutr.*, 8:480–490 (1960).

Muller, J.E. et al., "Circadian Variation in the Frequency of Sudden Cardiac Death," *Circulation*, 75:131–138 (1987).

Nagy, G. et al., "Untersuchungen über die Textur und die Eigenschaften von Acetylsalicylsäure–Tabletten 1. Mitteilung: Ein Fluβ der Herstellung–sweise auf die Eigenschaften der Tabletten," ("The texture and properties of acetylsalicylic acid tablets. 1. The effect of manufacturing methods on the properties of tablets") *Pharmazie*, 33(1):747–749 (1978). This document relates to the effect of manufacturing methods on the properties and textures of acetylsalicylic acid tablets.

Neuvonen, P.J., et al., "The Bioavailability of Sustained Release Nicotinic Acid Formulations," *Br. J. Clin. Pharmacol.*, 32:473–476 (1991).

Pinter, E.J. et al., "Biphasic Nature of Blood Glucose and Free Fatty Acid Changes Following Intravenous Nicotinic Acid in Man," *J. Clin. Endocrinol. Metab.*, 27:440–443 (1967).

Pintye–Hodi, K., et al., Untersuchungen über die Textur und die Eigenschaften von Acetylsalicysure–Tabletten 2. Mitteilung: Untersuchung der Textur durch Feuchtgranulierung bereiteter Tabletten, *Pharmazie*, 35(3):168–170 (1980) (with English translation of Abstract attached).

Rader, J.I., et al., "Hepatic Toxicity of Unmodified and Time–Release Preparations of Niacin," *Am. J. Med.*, 92:77–81 (1992).

Remington's Pharmaceutical Sciences, $15^{th}$ Ed., 1242–1251, Mack Publishing Co., Easton, PA. (1975).

Remington's Pharmaceutical Sciences, $18^{th}$ Ed., 1636–1637, Mack Publishing Co., Easton, PA (1990).

Remington's Pharmaceutical Sciences, 1304–1323; 1676–1686, Mack Publishing Co., Easton, PA, (1990).

Renzetti, A.R., et al., "Further Assessment of Glunicate Hypolipidaemic Activity in the Rat," *J. Pharm. Pharmacol.*, 37(12):906–909 (1985).

Ross, R., "The Pathogenesis of Atherosclerosis–An Update," *N. Engl. J. Med.*, 314(8):488–500 (1986).

Rowland, M., et al., *Clinical Pharmacokinetics: Concepts and Applications*, Les & Feiger, 111 (1980).

Salomon, J–L., et al., "Importance de la technologie et de la formulation pour le mécanism de libération du chlorure de potassium contenu dans des matrices hydrophiles 1. Influence de la viscosité et du pourcentage de gélifiant," ("Importance of technology and formulation for the mechanism of continuous liberation of potassium chloride from hydrophilic matrices. 1. Effect of viscosity and percentage of excipient") *Pharm ACTA Helv.*, 54(3):82–85 (1979) (with English translation of Abstract).

Salomon, J–L., et al., "Sustained Release of a Water–Soluble Drug from Hydrophilic Compressed Dosage Forms," *Pharm. Ind.*, 41(8):799–802 (1979).

Schlierf, G., et al., "Diurnal Patterns of Triglycerides, Free Fatty Acids, Blood Sugar, and Insulin During Carbohydrate–Induction in Man and Their Modification by Nocturnal Suppresion of Lipolysis," *J. Clin. Invest.*, 52:732–740 (1973).

Schlierf, G., et al., "Inhibition of Carbohydrate–Induced Hypertriglyceridemia by Nicotinic Acid," *Artery*, 3(2):174–179 (1977).

Schlierf, G., et al., "Diurnal Patterns of Plasma Triglycerides and Free Fatty Acids in Normal Subjects and in Patients with Endogenous (Type IV) Hyperlipoproteinemia," *Nutr. Metabol.*, 13:80–91 (1971).

Schlierf, G., et al., "Modification of 'Carbohydrate–Induced' Triglyceridemia by Nocturnal Suppression of Lipolysis — Comparison of Nicotinic Acid and Glucose," *Pharmacological Control of Lipid Metabolism, Proceedings of the Fourth International Symposium on Drugs Affecting Lipid Metabolism*, Philadelphia, PA, 26:319–320 (1971).

Schulman, K.A., et al., "Reducing High Blood Cholesterol Level With Drugs —Cost–effectiveness of Pharmacologic Management," *JAMA*, 264(23):3025–3033 (1990).

Shepherd, J., et al., "Effects of Nicotinic Acid Therapy on Plasma High Density Lipoprotein Subfraction Distribution and Composition and on Apolipoprotein A Metabolism," *J. Clin. Invest.*, 63:858–867 (1979).

Sokoloski, T.T., "Solutions and Phase Equilibria," *Remington's Pharmaceutical Sciences*, 17th Ed., 207–208, Mack Publishing Co., Easton, PA (1985).

Sprengers, E.D., et al., "Plasminogen Activator Inhibitors" *Blood*, 69(2):381–387 (1987).

Squires, R.W., et al., "Low–Dose, Time–Release Nicotinic Acid: Effects in Selected Patients With Low Concentrations of High–Density Lipoprotein Cholesterol," *Mayo Clin. Proc.*, 67(9):855–860 (1992).

Subissi, A., et al., "Acute Effects of Plasma Lipids in the Rat of a New Long–Acting Nicotinic Acid Derivative: LG 13979," *J. Pharm. Pharmacol.* 35:571–575 (1983).

Svedmyr, N., et al., "The Relationship between the Plasma Concentration of Free Nicotinic Acid and Some of Its Pharmacologic Effects in Man," *Clin. Pharm. Ther.*, 4(10):559–570 (1969).

Urberg, M., et al., "Evidence for Synergism Between Chromium and Nicotinic Acid in the Control of Glucose Tolerance in Elderly Humans," *Metabolism*, 36(9):896–899 (1987).

Urburg, M., et al., "Hypocholesterolemic Effects of Nicotinic Acid and Chromium Supplementation," *J. Family Practice*, 27(6):603–606 (1988).

Wahlberg, G., et al., "Effects of Nicotinic Acid on Concentrations of Serum Apolipoproteins B, C–1, C–II, C–III and E in Hyperlipidemic Patients," *Acta Med. Scand.*, 224:319–327 (1988).

Wiman, B., et al., "The Role of the Fibrinolytic System in Deep Vein Thrombosis," *J. Lab. Clin. Med.*, 105(2):265–270 (1985).

Complaint, filed by Kos Pharmaceuticals, Inc. against Barr Laboratories on Mar. 4, 2002, in Civil Action No. 02 CV 1683.

First Amended Complaint, filed by Kos Pharmaceuticals, Inc. on Mar. 11, 2002, in Civil Action No. 02 CV 1683.

Answer To First Amended Complaint, filed by Barr Laboratories on Mar. 25, 2002, in Civil Action No. 02 CV 1683.

Reply To Counterclaims, filed by Kos Pharmaceuticals, Inc. on Apr. 15, 2002, in Civil Action No. 02 CV 1683.

Amended Answer To First Amended Complaint, filed by Barr Laboratories on Aug. 19, 2002, in Civil Action No. 02 CV 1683.

Complaint, filed by Kos Pharmaceuticals, Inc. on Aug. 13, 2002, in Civil Action No. 02 CV 6409.

Answer To Complaint, filed by Barr Laboratories on Sep. 3, 2002, in Civil Action No. 02 CV 6409.

Complaint, filed by Kos Pharmaceuticals, Inc. on Nov. 12, 2002, in Civil Action No. 02 CV 8995.

Answer To Complaint, filed by Barr Laboratories on Dec. 3, 2002, in Civil Action No. 02 CV 8995.

Reply To Counterclaims And Counterclaims For Declaratory Judgment, filed by Kos Pharmaceuticals, Inc. on Mar. 4, 2003 in Civil Action No. 02 CV 8995.

\* cited by examiner

INTERMEDIATE RELEASE NICOTINIC ACID COMPOSITIONS FOR TREATING HYPERLIPIDEMIA

This United States patent application is a continuation-in-part of U.S. patent application Ser. No. 08/814,974, filed Mar. 6, 1997, now U.S. Pat. No. 6,129,930, which is a continuation-in-part of U.S. patent application Ser. No. 08/368,378, filed Jan. 14, 1995, now U.S. Pat. No. 6,080,428, which is a continuation-in-part of U.S. patent application Ser. No. 08/124,392, filed Sep. 20, 1993, now abandoned.

FIELD OF THE INVENTION

The present invention is directed to intermediate release nicotinic acid formulations having unique biopharmaceutical characteristics which are useful for treating hyperlipidemia, and methods of treating hyperlipidemia employing such compositions. Another aspect of the present invention, the nicotinic acid formulations are suitable for once a day dosing without causing drug-induced hepatotoxicity to a level which would require the therapy to be discontinued. More particularly, the present invention employs a composition of nicotinic acid, derivatives and mixtures thereof, and a swelling agent to form an intermediate timed-release sustaining composition for nocturnal or evening dosing. Specifically, the present invention employs a composition of nicotinic acid and hydroxypropyl methylcellulose to treat hyperlipidemia in a once per day oral dosage form given during the evening hours that causes little if any hepatotoxicity.

BACKGROUND

Nicotinic acid, 3-pyridinecarboxylic acid or niacin, is an antilipidemic agent that is marketed under, for example, the trade names Nicolar®, SloNiacin®, Nicobid® and Time Release Niacin®. Nicotinic acid has been used for many years in the treatment of lipidernic disorders such as hyperlipidemia, hypercholesterolemia and atherosclerosis. This compound has long been known to exhibit the beneficial effects of reducing total cholesterol, low density lipoproteins or "LDL cholesterol" triglycerides and apolipoprotein a (Lp(a)) in the human body, while increasing desirable high density lipoproteins or "HDL cholesterol".

Typical doses range from about 1 gram to about 3 rams daily. Nicotinic acid is normally administered two to four times per day after meals, depending upon the dosage form selected. Nicotinic acid is currently commercially available in two dosage forms. One dosage form is an immediate or rapid release tablet which should be administered three or four times per day. Immediate release ("IR") nicotinic acid formulations generally release nearly all of their nicotinic acid within about 30 to 60 minutes following ingestion, as illustrated in FIG. 1. The other dosage form is a susained release form which is suitable for administration two to four times per day. See, however, U.S. Pat. No. 5,126,145 issued to O'Neill. In contrast to IR formulations, sustained release ("SR") nicotinic acid formulations are designed to release significant quantities of drug for absorption into the blood stream over specific timed intervals, also as shown in FIG. 1. If the release occurs at appropriate times, therapeutic levels will be maintained by SR nicotinic acid formulations over an extended period such as 12 or 24 hours after ingestion.

The dosing regimen of IR nicotinic acid is known to provide a very beneficial effect on blood lipids as discussed in Knopp et al.; "Contrasting Effects of Unmodified and Time-Release Forms of Niacin on Lipoproteins in Hyperlipidemic Subjects: Clues to Mechanism of Action of Niacin"; Metabolism 34/7, 1985, page 647. The chief advantage of this profile is the ability of IR nicotinic acid to decrease total cholesterol, LDL cholesterol, triglycerides and Lp(a) while increasing HDL particles. In fact, IR nicotinic acid has been well regarded as an effective drug in the treatment of high cholesterol since about the early 1960s. Unfortunately, IR nicotinic acid has never really become widely used because of the high incidence of flush that often occurs when an IR dose is taken. That means an individual may develop a visible, uncomfortable, hot or flushed feeling three or four times a day for about one hour following each IR dose.

In order to avoid or reduce the cutaneous flushing, a number of materials have been suggested for administration with an effective antihyperlipidemic amount of immediate release nicotinic acid, including guar gum in U.S. Pat. No. 4,956,252, and mineral salts as disclosed in U.S. Pat. No. 5,023,245; or inorganic magnesium salts as reported in U.S. Pat. No. 4,911,917. These materials have been reported to avoid or reduce the cutaneous flushing side effect commonly associated with nicotinic acid treatment.

Another method of avoiding or reducing the side effects associated with immediate release nicotinic acid is the use of SR nicotinic acid formulations. SR nicotinic acid formulations are designed to slowly release the compound from the tablet or capsule. The slow drug release reduces and prolongs blood levels of drug in an attempt to lower peak nicotinic acid concentrations with the goal of reducing or eliminating nicotinic acid induced flush. Examples of currently marketed SR formulations of nicotinic acid include Nicobid® capsules (Rhone-Poulenc Rorer), Enduracin® (Innovative Corporation) and SloNiacin® (Upsher-Smith Laboratories, Inc., U.S. Pat. No. 5,126,145 which describes a sustained release niacin formulation containing two different types of hydroxypropyl methylcellulose and a hydrophobic component).

Studies in hyperlipidemic patients have been conducted with a number of SR nicotinic acid products. These studies have demonstrated that the sustained release products do not have the same advantageous lipid altering effects as IR nicotinic acid, and in fact often have a worse side effect profile compared to the IR products. The major disadvantage of the SR formulations, as can be seen in Knopp et al., in 1985, is the significantly lower reduction in triglycerides (−2% for the sustained release versus −38% for the immediate release) and lower increase in HDL cholesterol, represented as $HDL_2$ particles which are known by the art to be most beneficial, (−5% for the sustained release versus +37% for the immediate release).

Additionally, SR nicotinic acid formulations have been noted as causing greater incidences of liver toxicity as described in Henken et al.: Am J Med, 91:1991 (1991) and Dalton et al.: Am J Med, 93:102 (1992). There is also great concern regarding the potential of these formulations in disrupting glucose metabolism and uric acid levels.

In a recent edition of the Journal of the American Medical Association, an article appeared which presented research results investigating the liver toxicity problems associated with an SR form of nicotinic acid. See McKenney et al.: A Comparison of the Efficacy and Toxic Effects of Sustained- vs. Immediate-Release Niacin in Hypercholesterolemic Patients, JAMA, (271)9: 672 (Mar. 2, 1994). This McKenney et al. article presented a study of twenty-three patients. Of that number, 18 or 78 percent were forced to withdraw because liver function tests (LFTs) increased indicating potential liver damage. The conclusion of the authors of that article was that the SR form of nicotinic acid "should be restricted from use."

A similar conclusion was reached in an article authored by representatives of the Food and Drug Administration. See Radar, et al.: Hepatic Toxicity of Unmodified and Time-Release Preparations of Niacin, *JAMA*, 92:77 (January 1992). Because of these studies and similar conclusions drawn by other health care professionals, the sustained release forms of nicotinic acid have experienced limited utilization.

Consistent with these conclusions, certain IR formulations are FDA approved for the treament of hyperlipidemia. The SR products, however, are not FDA approved for the treatment of hyperlipidemia and may only be marketed as over-the-counter nutritional supplies. As over-the-counter nutritional supplements, SR nicotinic acid formulations are not subject to the rigorous FDA imposed in vivo and in vitro testing required of prescription SR products. Rather, anyone can market an SR nicotinic acid product as a nutritional supplement as long as it is manufactured using "Good Manufacturing Procedures." Notwithstanding their commercial availability in the United States, many investigators have recommended that the SR nicotinic acid products be removed from non-prescription status because of their incidence of hepatotoxicity and the lack of sufficient medical testing to support their marketing. See Dalton, T. A. et al.: *Am J Med*, (93):102–104 (1992); Etchason, J. A. et al.: *Mayo Clin Proc*, (66):23–28 (1991); and Fischer, D. J. et al.: *Western J. Med.*, (155)4:410–412 (1991).

In designing an SR nicotinic acid product, the pharmacokinetics can have a considerable impact on whether a particular SR nicotinic acid will produce satisfactory results after in vivo administration. Orally administered drugs, such as nicotinic acid, are absorbed and enter the capillaries and veins of the upper GI tract and are transported by the portal vein directly to the liver before entering the general circulation of the body. The entire absorbed drug is exposed to the liver during its first pass through the body. If a drug is subject to a high hepatic clearance, i.e., it is rapidly metabolized by the liver, then a substantial fraction of the absorbed dose is extracted from the blood and metabolized before it reaches the systemic circulation. This phenomenon is characterized as the "first pass effect." The consequence of this phenomenon is a significant reduction in bioavailability. In some instances, the first pass effect is so large as to render oral administration of a drug ineffective.

Figure 2:
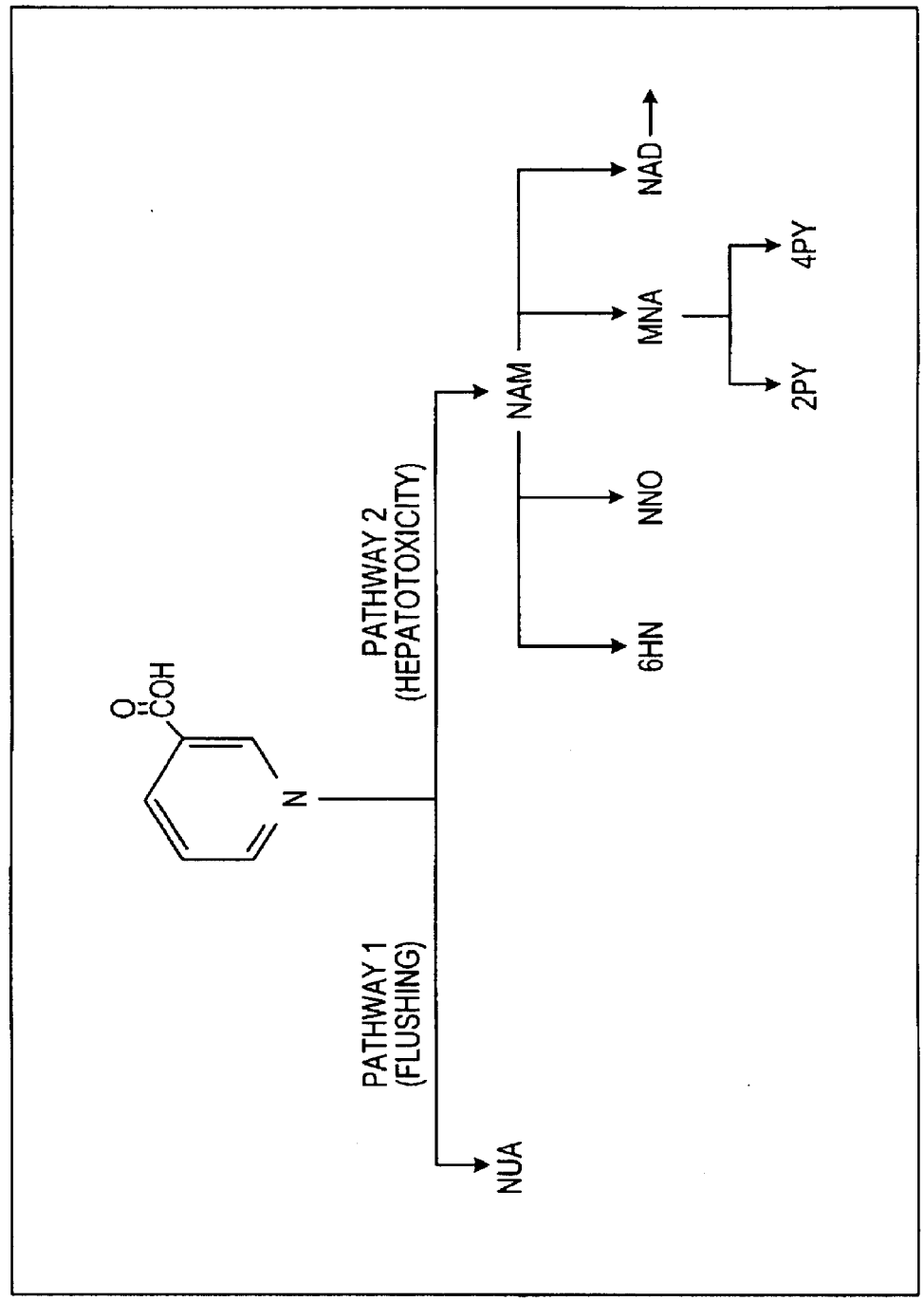

The pharmacokinetics of nicotinic acid have been some what studied in the past. Nicotinic acid is well absorbed from the gastrointestinal tract and is subjected to an extensive first pass effect. More particularly, nicotinic acid is metabolized into many by products as depicted in FIG. 2 and undergoes saturable first pass metabolism resulting into two metabolic pathways. Pathway 2 is the saturable pathway, whereas Pathway 1 is the secondary metabolic process that is initiated only after all of the enzymes in Pathway 2 are occupied or "saturated." In other words, as the concentration of nicotinic acid accumulates or backs up due to the "saturation" of the enzymes in Pathway 2, the secondary metabolic process, i.e., Pathway 1, is initiated. The nicotinic acid metabolites produced in both pathways are common to all nicotinic acid formulations either IR or SR. As shown in FIG. 2, Pathway 1 includes nicotinic acid and nicotinuric acid ("NUA"), and Pathway 2 includes the phase I metabolites, nicotinamide ("NAM"), 6-hydroxy nicotinamide ("6HN"), nicotinamide-N-oxide ("MNO"), N-methyl-nicotinamide ("MNA") and nicotinamide adenine dinucleotide ("NAD"). As further shown in FIG. 2, Pathway 2 includes the metabolites of MNA, N-methyl-2-pyridone-5-carboxamide (2PY) and N-methyl-4-pyridone-5-carboxamide (4PY), and the entire NAD cycle which is necessary in nearly all biochemical processes within the cells.

Compounds such as nicotinic acid which are subject to a first pass metabolism are considered to have nonlinear pharmacokinetics. An increase or decrease in the dose administered will not necessarily produce the corresponding increase or decrease in observed blood levels. This is believed to be dependent upon whether the metabolic level of the liver has been exceeded. Therefore, it is thought that the percent of administered nicotinic acid dose metabolized before the compound leaves the liver is dependent upon the dose administered and the release rate.

It has been long appreciated by those of skill in the art that it can be difficult to design SR formulations for compounds, like nicotinic acid, that are subjected to the first pass effect. See Urquhart et al.: Controlled-Release Pharmaceuticals, *Am Pharm Assoc*, (1979). Whereas an IR product allows saturation of the enzymes and a significant increase in blood levels, an SR product releasing similar quantities of drug at a slow rate will typically either not produce saturation of the primary metabolic pathway or only initiate the secondary metabolic process to a minimal extent. Consequently, a larger percentage of an SR dose will be metabolized before it has had an opportunity to dear the liver. Moreover, the particular time at which a drug should be released varies significantly with each drug and is dependent upon its pharmacokinetics. The difficulty of correctly predicting an appropriate release pattern is well known to those skilled in this art.

Therefore, it would be a valuable contribution to the art to develop an extended release nicotinic acid formulation for once a day nocturnal administration for approval by the FDA which would provide hyperlipidemic individuals with "balanced lipid alteration," i.e., reductions in total cholesterol, LDL cholesterol, triglycerides and Lp(a) as well as increases in HDL particles, with an acceptable safety profile, especially as regards to liver toxicity and effects on glucose metabolism and uric acid levels.

SUMMARY OF THE INVENTION

In brief, the present invention alleviates and overcomes certain of the above-identified problems and shortcomings of the present state of nicotinic acid therapy through the discovery of novel nicotinic acid formulations and methods of treatment.

Generally speaking, novel nicotinic acid formulations have been discovered that optimize blood levels of nicotinic acid over a period of about 5 to about 9 hours when administered as a single oral dose for achieving a balanced lipid alteration in individuals at a time when the rate of serum lipids, lipoproteins, cholesterol and cholesterol precursor biosynthesis is believed to be at its highest. In other words, the novel nicotinic acid formulations have been uniquely formulated for administration as a single dose, preferably during the evening or at night when the nicotinic acid levels subsequently achieved are effective for substantially lowering the levels of total cholesterol, LDL cholesterol, triglycerides and/or Lp(a) as well as raising the levels of HDL particles, all of which are primarily nocturnally synthesized. Preferably, the nicotinic acid formulations are administered at or after an evening meal or low fat snack but before bedtime, i.e., between about 6 pm and 12 am, preferably between about 8 pm and 12 am, and most preferably between about 8 pm and 10 pm.

The amount of nicotinic acid that is administered is effective to substantially lower at least one serum lipid, such as total cholesterol, LDL cholesterol, triglycerides, and/or Lp(a) and elevated HDL-C, without causing drug-induced hepatotoxicity to levels which would require the therapy to be discontinued. In other words, a single 1 to 3 gram dose of a nicotinic acid formulation of the present invention administered between about 6 pm and 12 am is believed to be as effective as an equal or higher daily dosage of nicotinic acid administered in two to four divided doses between, e.g., 8 am and 8 pm.

Furthermore, because at least the majority of the nicotinic acid is released and metabolized to in vivo during a limited predetermined period of time of about 5 to about 9 hours, the liver is not being exposed to constant levels of nicotinic acid which results during the administration of long-term, spaced daily doses of SR nicotinic acid. Thus, it is believed that the nicotinic acid formulations of the present invention are unlikely to cause individuals to develop dose-limiting hepatotoxicity when used as a single daily dose administered in a therapeutic amount.

The nicotinic acid formulations in accordance with the present invention have been uniquely designed as intermediate release formulations which can be characterized by one or more of the following biopharmaceutic charcteristics: (1) an in vivo stair-stepped or sigmoidal-shaped absorption profile when the plasma nicotinic acid or NUA data is deconvoluted using the Wagner-Nelson method, (2) an in vitro dissolution profile; (3) a fit factor $F_2$; (4) urine metabolite recovery; (5) AUC; (6) Cmax; and/or (7) Tmax. By the term "intermediate release," it is used herein to characterize the nicotinic acid formulations of the present invention which release their medication in vitro or in vivo over a period of time which is greater than about 1 to 2 hours, i.e., slower that IR niacin, but less than about 10 to 24 hours, i.e., faster than SR niacin.

It is therefore, an object of the present invention to provide a composition of nicotinic acid or any compound which is metabolized by the body to form nicotinic acid for treating hyperlipidemia.

It is another object of the present invention to provide a composition as above, which as a time release sustaining characteristic.

It is yet another object of the present invention to provide a method for employing a composition as above, for treating hyperlipidemia, which results in little or no liver damage.

At least one or more of the foregoing objects, together with the advantages thereof over the known art relating to the treatment of hyperlipidemia, which shall become apparent from the specification which follows, are accomplished by the invention as hereinafter described and claimed.

In general, the present invention provides an improved antihyperlipidemia composition of the oral type employing an effective antihyperlipidemic amount of nicotinic acid, wherein the improvement comprises compounding the nicotinic acid with from about 5% to about 50% parts by weight of hydroxypropyl methylcellulose per hundred parts by weight of table or formulation.

The present invention also provides an orally administered antihyperlipidemia composition which comprises from about 30% to about 90% parts by weight of nicotinic acid; and, from about 5% to about 50% parts by weight of hydroxypropyl methylcellulose.

Generally speaking, the nicotinic acid formulations of the present invention are manufactured by first wet mixing (granulation) niacin and hydroxypropyl methylcellulose, the immediate-release excipient, in a high-energy, high-shear mixer to produce dense niacin pellets. The pellets are then mixed with more hydroxypropyl methylcellulose and compressed into tablets. The resulting tablets are then formed by a mixture of hydroxypropyl methylcellulose-niacin granulation and additional hydroxypropyl methylcellulose.

The present invention also includes a method of treating hyperlipidemia in a hyperlipidemic. The method comprises the steps of forming a composition which comprises an effective antihyperlipidemic amount of nicotinic acid and an amount of excipients to provide intermediate release of drug. The method also includes the step of orally administering the composition to the hyperlipidemic nocturnally.

A method of treating hyperlipidemia in a hyperlipidemic according to the invention, comprises dosing the hyperbpidemic with an effective antihyperlipidemic amount of nicotinic acid or compound metabolized to nicotinic acid by the body. The dose is given once per day in the evening or at night, combined with a pharmaceutically acceptable carrier to produce a significant reduction in total and LDL cholesterol as well as significant reduction in triglycerides and Lp(a), with a significant increase in HDL cholesterol.

Once the niacin formulations of the present invention are swallowed or consumed, the tablets become wet and the hydroxypropyl methylcellulose surrounding the tablets is believed to form thin gel layers. Any granular nicotinic acid exposed to the exteriors of the tablets will dissolve out of the tablets resulting in an intermediate rate of nicotinic acid for absorption. As the nicotinic acid leaves the outer surfaces of the tablets, gastrointestinal fluid can reach deeper into the tablets resulting in thicker gel layers and the dissolution of the intermediate release nicotinic acid granules surrounded by the gel layers. The gel layers then act as controlled release layers for dissolved nicotinic acid originating in the intermediate release nicotinic acid granules.

The above features and advantages of the present invention will be better understood with reference to the following FIG., detailed description and examples. It should also be understood that the particular methods and formulations illustrating the present invention are exemplary only and not to be regarded as limitations of the present invention.

DESCRIPTION OF THE FIGS.

Figure 3:
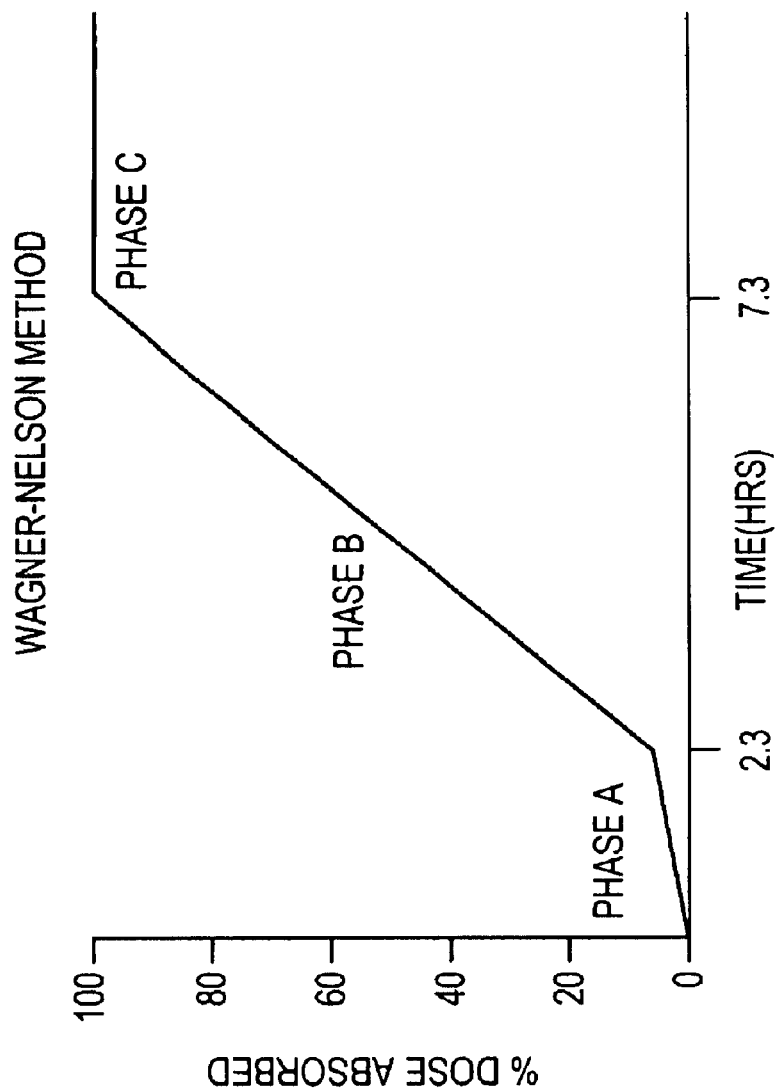
Figure 4:
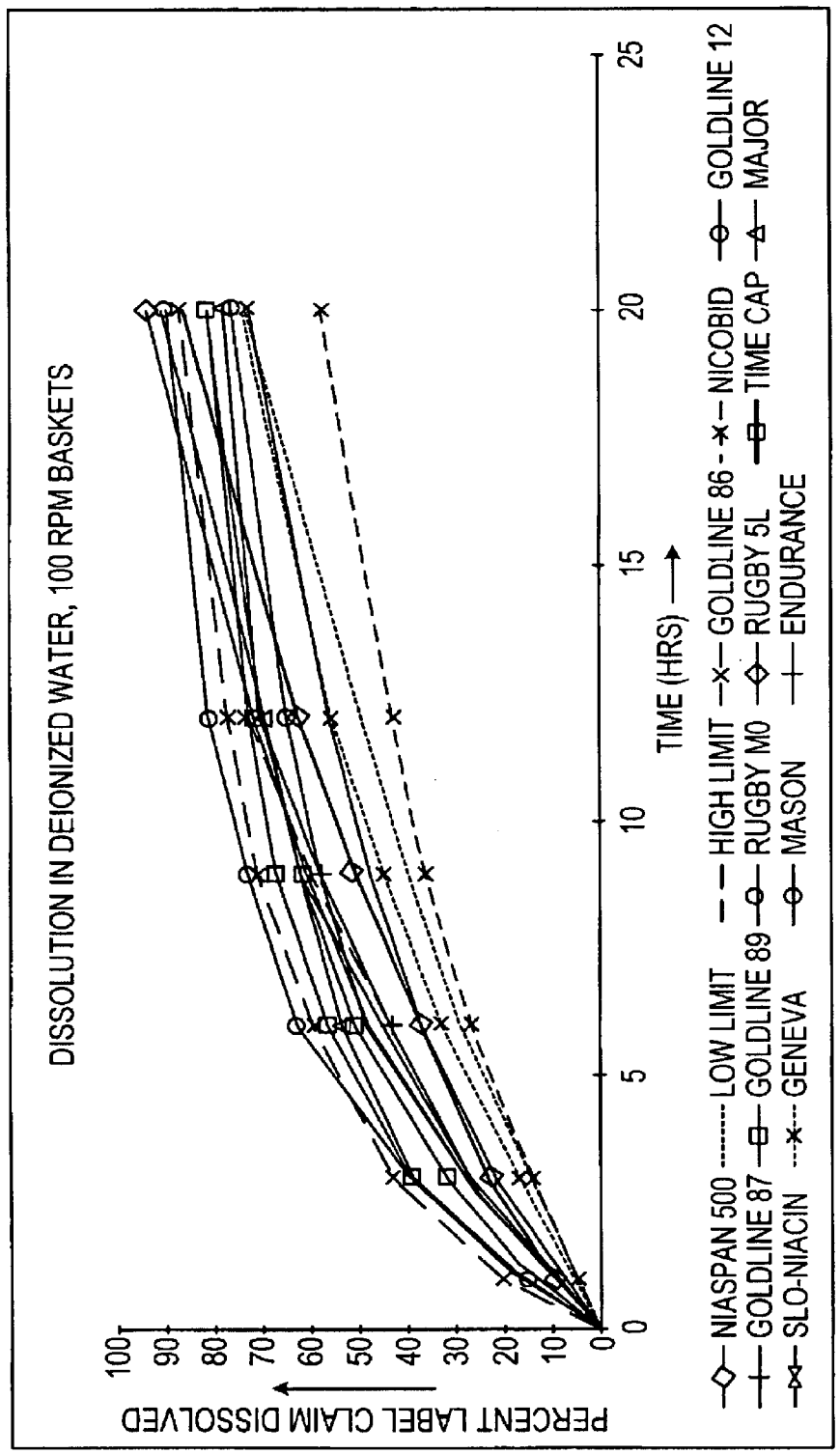
Figure 5:
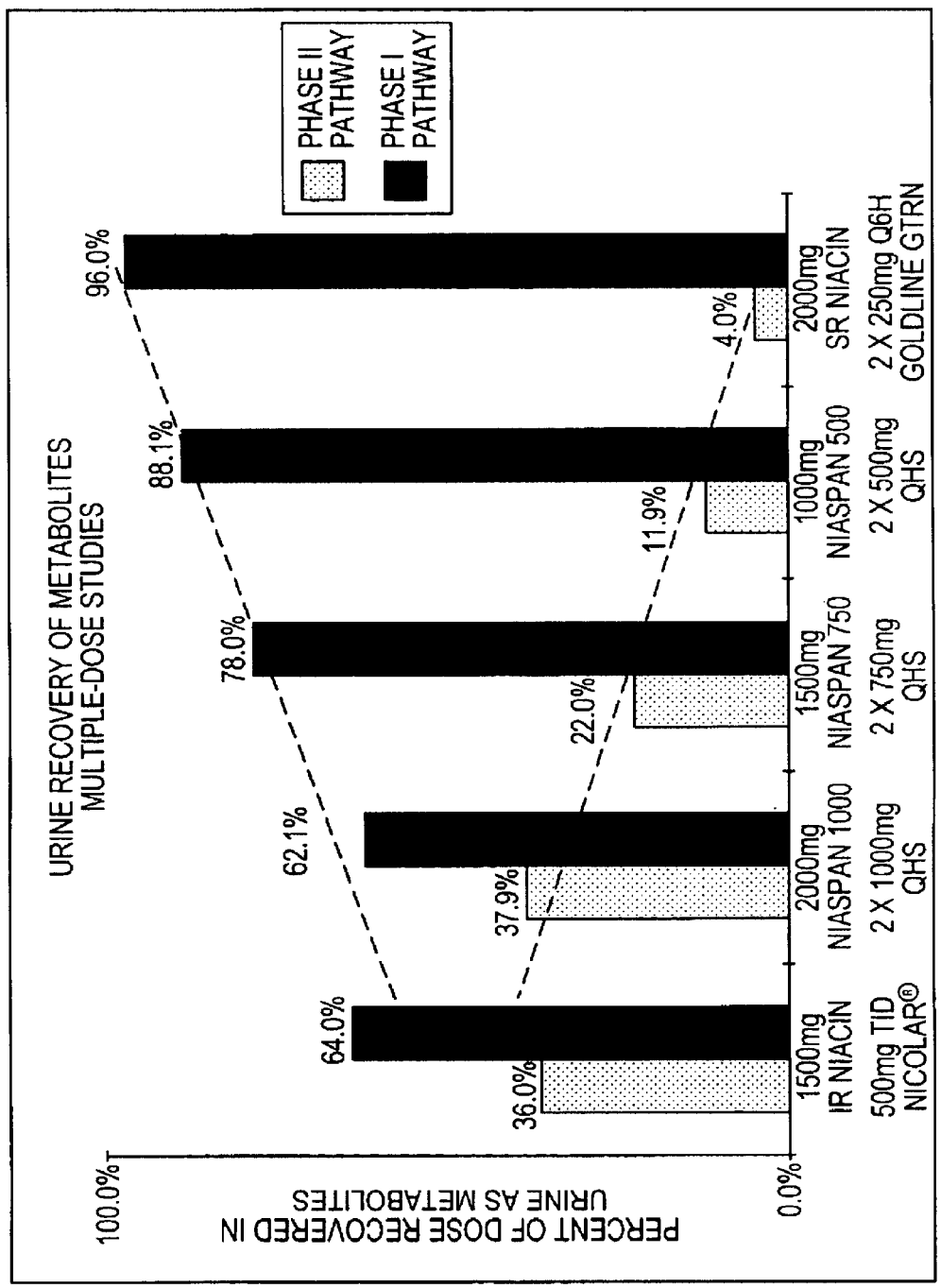
Figure 5:
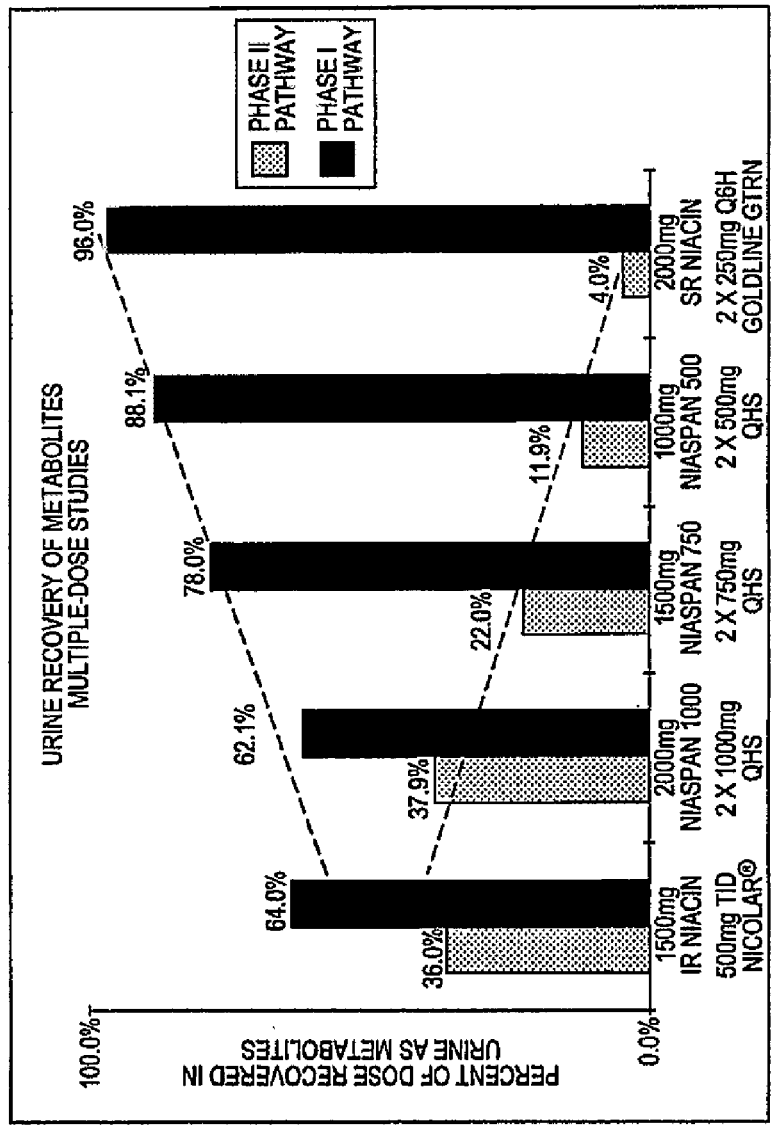

With reference to the accompanying Figs., which are illustrative of certain embodiments within the scope of this invention:

FIG. 1 is a graph depicting the typical in vito dissolution profiles of an immediate release niacin formulation and a sustained release niacin formulation;

FIG. 2 is a schematic depicting the metabolic pathways of niacin in the liver and the niacin metabolites that are common to all niacin formulations, including the immediate and sustained release formulations. Pathway 1 includes niacin and nicotinuric acid (NUA) and Pathway 2 includes the Phase I metabolites, nicotinamide ("NAM"), 6-hydroxy nicotinamide ("6HN"), nicotinamide-N-oxide ("MNO"), N-methyl-nicotinamide ("MNA") and nicotinamide adenine dinucleotide ("NAD"). FIG. 2 also depicts that Pathway 2 includes the metabolites of MNA, N-methyl-2-pyridone-5-carboxamide (2PY) and N-methyl-4-pyridone-5-carboxamide (4PY), and the entire NAD cycle which is necessary in nearly all biochemical processes within the cells;

FIG. 3 is a graph depicting an in vivo stair-stepped or sigmoidally-shapedabsorption profile or curve which has been deconvoluted using the Wagner-Nelson method from the mean of plasma cuves for niacin released from Niaspan® formulations of the instant invention. The profile shows that niacin is absorbed at a lesser rate during about the first two hours and at a significantly faster rate between about hours 2 and 7 following ingestion. The profile also shows that approximately 100% A of the absorbable niacin is absorbed at about 7.3 hours after ingestion;

FIG. 4 is a graph depicting individual in vitro dissolution profiles of a Niaspan® formulation and thirteen (13) commercially available sustained release niacin formulations; and FIG. 5 is a chart depicting the percent of a niacin dose recovered in urine as metabolites following consumption of a dose of 500 mg of Nicolar®, an immediate release niacin product, doses of 2000 mg, 1500 mg and 1000 mg of Niaspan®, and a dose of 2000 mg of Goldline's time released niacin, a sustained release product. The Phase I pathway concerns those metabolites that are generated by the oxidative pathway. The Phase II pathway includes niacin and nicotinuric acid (NUA) metabolites. The chart shows that a 1500 mg dose of Niaspan® produces less Phase II pathay metabolites than a 1500 mg dose of an immediate release niacin formulation, i.e., Nicolar®. The chart also shows that a 2000 mg dose of Niaspan® produces less Phase I pathway oxidative metabolites than a similar dose of a sustained release niacin product, i.e., Goidline's timed release niacin.

DETAILED DESCRIPTION OF THE INVENTION

By way of illustrating and providing a more complete appreciation of the present invention and many of the attendant advantages thereof, the following detailed description and examples are given concerning the novel methods and formulations.

Turning now to the biopharmaceutic characteristics of the novel nicotinic acid formulations, the nicotinic acid formulations of the present invention exhibit an in vivo stair-stepped or sigmoidal-shaped profile when the plasma cuves for nicotinic acid or NUA are deconvoluted using the Wagner-Nelson method, as taught in Wagner, J. G. et al.: *J Pharm Sciences,* 52:610–611 (1963), which is incorporated herein by reference in its entirety. As illustrated in FIG. 3, the stair-stepped or sigmoidal-shaped time plot for nicotinic acid absorbed from the formulations of the instant invention is characterized by three phases, designated as phases A, B and C, and by the fact that significant quantities of nicotinic acid are absorbed from such formulations during phases A and B, and predominantly during phase B. Phase A constitutes the initial time period where minimal absorption of nicotinic acid occurs, whereas phase B represents the period time that follows phase A where most of the absorption of nicotinic acid occurs. Phase C concerns that period of time when absorption of nicotinic acid generally ends.

In accordance with the present invention, phase A generally occurs at from about 1 to about 4 hours with a mean of about 2.3 hours after ingestion, and phase B generally occurs for about 4 to about 8 hours with a mean of about 5 hours after phase A. Phase C generally occurs at about 5 to about 9 hours with a mean of about 7.3 hours after ingestion. See Tables 1 and 2. Also reported in Table 1, up to about 19% and preferably about 6.4% is absorbed during phase A, between about 78% and 100% and preferably about 90% is absorbed during phase B, with the remainder, if any, being absorbed during phase C.

As indicated above, deconvolution is calculated using the Wagner-Nelson method of plasma niacin or NUA data generated from frequent blood sampling following the administration of the formulations of the present invention to healthy human volunteers resulting in a percent absorbed time plot which is described in three phases:

Phase A—the initial time period where minimal absorption occurs;

Phase B—the subsequent time period where most of the absorption occurs; and

Phase C—the time when absorption has ended.

The expected values describig each Phase are recited in Table 1:

TABLE 1

|  | Start (hrs) | Start range (hrs) | % Dose Absorbed/hr | Absorption rate range | End (hrs) | End range (hrs) | % Dose Absorbed | % Dose Absorbed Range (%/hr) |
|---|---|---|---|---|---|---|---|---|
| Phase A | 0 | NA | 3.3 | 0–9.2 | 2.3 | 1.1–4.1 | 6.4 | 0–1.91 |
| Phase B | 2.3 | 1.1–4.1 | 19.0 | 14.1–26.1 | 7.3 | 5.1–9.1 | 90.7 | 78.4–100.4 |
| Phase C | 7.3 | 5.1–9.1 | 0 | 0 | NA | NA | 97.1 | 85.7–103.7 |

Table 2 represents the absorption rate parameters of nicotinic acid in 12 individuals, who each ingested two, 1000 mg tablets of Niaspan®, and the minimum, maximum, mean and median for each of those 12 individuals tested. Table 1 is a summary of the results in Table 2.

TABLE 2

| Subject | First Absorption Rate (% Dose/Hr) | End First Absorption Phase (hr) | Second Absorption Rate (% Dose/Hr) | End Second Absorption Phase (hr) |
|---|---|---|---|---|
| 1 | 1.90 | 4.08 | 21.82 | 8.08 |
| 2 | 4.07 | 2.08 | 15.86 | 8.08 |
| 3 | 5.55 | 2.08 | 20.94 | 6.08 |
| 4 | 4.39 | 1.08 | 15.57 | 7.08 |
| 5 | 9.16 | 2.08 | 26.12 | 5.08 |
| 6 | 4.07 | 1.08 | 23.22 | 5.08 |
| 7 | 0.00 | 3.08 | 14.28 | 9.08 |
| 8 | 3.24 | 2.08 | 18.08 | 7.08 |
| 9 | 0.00 | 2.08 | 25.10 | 6.08 |
| 10 | 0.00 | 2.08 | 16.21 | 8.08 |
| 11 | 6.96 | 2.08 | 14.09 | 8.08 |
| 12 | 0.00 | 3.08 | 16.54 | 9.08 |
| Mean | 3.28 | 2.25 | 18.99 | 7.25 |
| Minimum | 0.00 | 1.03 | 14.09 | 5.08 |
| Maximum | 9.16 | 4.08 | 26.12 | 9.08 |
| Median | 3.65 | 2.08 | 17.31 | 7.58 |

The unique nicotinic acid formulations of the present invention therefore result in subsequently all of the nicotinic acid being absorbed within about 5 to about 9 hours, preferably between about 6 and about 8 hours and most preferably between about 7 and 8 hours, following ingestion.

Minimal nicotinic acid is absorbed thereafter. It is believed that Phase A results in the plasma concentration of nicotinic acid or NUA prior to the saturation of Pathway 2, whereas phase B concerns the plasma concentration of nicotinic acid or NUA afer Pathway 2 has been saturated. It is further believed that the stair-stepped or sigmoidal-shape developed for NUA are as reliable as that developed for nicotinic acid, since the Tmax and shape of the plasma curve parallels the Tmax and shape of the plasma curve for nicotinic acid. The initial absorption of nicotinic acid allows for the initial obtainment of therapeutic levels of nicotinic acid and the second absorption period, phase B, optimizes therapeutic levels thereafter.

Each nicotinic acid formulation of the instant invention will typically exhibit the following dissolution profile in U.S.P.XXIII, Apparatus I, 900 mls of deionized water at 37° C., baskets at 100 RPM, as indicated in Table 3.

TABLE 3

| Time (hours) | Niaspan ® Specification Percent Dissolved | Dissolution range for all Niaspan ® strengths tested in humans | Dissolution range for FDA approved Niaspan ® tablet batches for all strengths |
|---|---|---|---|
| 0 | 0 | 0 | 0 |
| 1 | less than 15 | 9.6–13.8 | 9.8–12.3 |
| 3 | 15–30 | 21.2–27.8 | 20.9–26.7 |
| 6 | 30–45 | 35.1–44.2 | 35.3–44.1 |
| 9 | 40–60 | 45.6–58.5 | 44.8–58.7 |
| 12 | 50–75 | 56.2–72.0 | 59.5–70.7 |
| 20 | greater than 75 | 78.1–103.9 | 84.4–120.5 |

By the term "dissolution," it is used herein to refer to that percent of a drug, e.g., nicotinic acid, which is dissolved or released in vitro from a formulation into a dissolution medium over a selected period of time under certain conditions. With respect to the shape of the dissolution curve concerning the specifications in Table 3 relative to a target dissolution curve for each Niaspan® tablet strength, the target dissolution curve for each of the Niaspang tablet strengths are as follows:

TABLE 4

| Time (hours) | 250 and 325 mg (% released) | 500 mg (% released) | 750 mg (% released) | 1000 mg (% released) |
|---|---|---|---|---|
| 0 | 0 | 0 | 0 | 0 |
| 1 | 11.3 | 10.6 | 10.3 | 11.8 |
| 3 | 24.1 | 22.9 | 22.0 | 25.5 |
| 6 | 40.2 | 38.0 | 36.60 | 41.3 |
| 9 | 54.2 | 51.4 | 49.4 | 54.8 |
| 12 | 67.0 | 63.4 | 61.6 | 66.3 |
| 20 | 91.7 | 88.4 | 87.2 | 98.4 |

It is believed that the nicotinic acid formulations of the present invention are responsible for a controlled absorption profile that is intermediate to that of IR and SR nicotinic acid formulations currently comercially available. As depicted in FIG. 4 and Tables 3, 4, 5A and 5B, and especially Tables 5A and 5B, the dissolution profile of the nicotinic acid formulations of the present invention, i.e., Niaspan®, is slower than that of IR niacin, but different than that of SR niacin commercially available products. The uniqueness of the dissolution profile for the nicotinic acid formulations of the present inventions is shown in FIG. 4 and Tables 3,4, 5A and 5B.

Tables 5A and 5B depict dissolution data for two representative lots of Niaspan® 500 mg tablet strength and other commercially available SR nicotinic acid 500 mg products. The dissolution data of Table 5 represents two lots of Niaspang 500 mg tablets which fall within the range of the dissolution profile provided for Niaspan® tablets of the present invention. Also as illustrated in FIG. 4 and Tables 3, 4 and 5A and 5B, and in particular Tables 5A and 5B, when the dissolution profiles of sixteen (16) over-the-counter SR niacin products are compared to that of Niaspan®, none of the dissolution curves for those products are equivalent to that of Niaspan®.

TABLES 5A and 5B

Brand Comparison

TABLE 5A

| Time hrs | Niaspan ® 500 mg | Niaspan ® K4061A-1 500 mg | Low Limit | High Limit | Goldline 86 86A6014C 250 mg | Nicobid MN0928 500 mg | Goldline 12 12L51229 500 mg | Goldline 87 87L51081 500 mg | Goldline 89 89G5612C 500 mg | Rugby MO M070E 500 mg | Rugby SL 5L01707 500 mg | Time Cap A051 500 mg |
|---|---|---|---|---|---|---|---|---|---|---|---|---|
| 0 | 0 | 0 | — | — | 0 | 0 | 0 | 0 | 0 | 0 | 0 | 0 |
| 1 | 10.3 | 10.8 | | 15 | 5.4 | 4.9 | 12.6 | 10.8 | 16.5 | 16.7 | 11.7 | 14.9 |
| 3 | 22.5 | 23.9 | 15 | 30 | 16.9 | 14.4 | 28.0 | 26.5 | 39.0 | 40.6 | 27.1 | 32.4 |
| 6 | 37.6 | 39.0 | 30 | 45 | 32.9 | 26.9 | 47.8 | 43.9 | 57.3 | 62.9 | 46.1 | 50.6 |
| 9 | 51.2 | 51.8 | 45 | 60 | 42.9 | 37.0 | 58.8 | 58.0 | 67.3 | 73.0 | 60.4 | 62.9 |
| 12 | 62.8 | 63.1 | 50 | 75 | 56.0 | 43.9 | 65.7 | 69.4 | 73.0 | 81.7 | 72.2 | 70.3 |
| 20 | 87.1 | 85.2 | 75 | | 72.8 | 58.3 | 77.0 | 91.7 | 81.6 | 89.3 | 94.3 | 81.3 |

TABLE 5B

| Time hrs. | Niaspan ® 500 mg | Niaspan ® K4061A-1 500 mg | Low Limit | High Limit | Major 5F00753 500 mg | Upsher-S 16020 500 mg | Geneva 4B124 500 mg | Mason 501199 500 mg | Endurance 11504 500 mg | Rugby K053G 500 mg | Nicobid MN1937 500 mg | Goldline 89A51566 500 mg |
|---|---|---|---|---|---|---|---|---|---|---|---|---|
| 0 | 0 | 0 | — | — | 0 | 0 | 0 | 0 | 0 | 0 | 0 | 0 |
| 1 | 10.3 | 10.8 | | 15 | 16.6 | 13.7 | 20.7 | 11.3 | 11.0 | 31.9 | 10.8 | 11.0 |
| 3 | 22.5 | 23.9 | 15 | 30 | 38.7 | 28.1 | 43.2 | 27.1 | 24.2 | 42.2 | 27.2 | 30.6 |
| 6 | 37.6 | 39.0 | 30 | 45 | 53.7 | 45.7 | 60.0 | 45.4 | 36.5 | 61.0 | 38.1 | 53.2 |
| 9 | 51.2 | 51.8 | 45 | 60 | 61.7 | 61.4 | 71.5 | 60.4 | 48.1 | 72.9 | 51.5 | |

TABLE 5B-continued

| Time hrs. | Niaspan® 500 mg | Niaspan® K4061A-1 500 mg | Low Limit | High Limit | Major 5F00753 500 mg | Upsher-S 16020 500 mg | Geneva 4B124 500 mg | Mason 501199 500 mg | Endurance 11504 500 mg | Rugby K053G 500 mg | Nicobid MN1937 500 mg | Goldline 89A51566 500 mg |
|---|---|---|---|---|---|---|---|---|---|---|---|---|
| 12 | 62.8 | 63.1 | 50 | 75 | 70.6 | 73.5 | 77.8 | 71.0 | 56.4 | 77.9 | 61.1 | 74.7 |
| 20 | 87.1 | 85.2 | 75 | | 78.3 | 92.8 | 87.6 | 90.5 | 71.9 | 84.0 | 75.9 | 85.6 |

Similarity between the test and the target dissolution curves within a tablet strength can be determined through the calculation of the fit factor $F_2$. See Moore J W, Flanner H H.: Mathematical comparison of dissolution profiles, *Pharmaceutical Technology*, 64–74 (June 1996), which is incorporated herein by reference in its entirety. In other words, the fit factor $F_2$ is calculated using the difference between the percent dissolved at each time point for each dissolution profile. If there is no difference between the percent dissolved at each time point, the fit factor $F_2$ equals 100. As the difference in percent dissolved increases, however, the fit factor $F_2$ value decreases. The fit factor $F_2$ is determined by the following equation:

$$F_2 = 50 \log \left\{ \left[ 1 + 1/n \sum_{i=1}^{n} w_t(R_t - T_t)^2 \right]^{-0.5} \times 100 \right\}$$

where $R_t$ is the dissolution value for the target profile at a time point t, $T_t$ is the dissolution value for the test profile at the same time point t, n is the number of time points on the dissolution profile and $w_t$ is an optional weight factor. This equation is a logarithmic transformation of the sum of the mean square error between the test and target profile, resulting in a number between 0 and 100. The fit factor $F_2$ is 100 when two dissolution profiles are identical and decreases as the two profiles become more dissilimar. In other words, the smaller the fit factor $F_2$, the farther apart the products are from one another. The fit factor $F_2$ will be positive as long as the average difference between the two curves is 100 or less.

The following Table 6 depicts the recommended fit factor $F_2$ values for each of the Niaspan® tablet strengths. The recommended values are based on the range of fit factors $F_2$ between lots used in the New Drug Application (NDA), made more specific by the determination of bioequivalence to a target lot of Niaspan® tablets.

TABLE 6

| Criteria derived from: | 250 and 325 mg tablet strengths | 500 mg tablet strength | 750 mg tablet strength | 1000 mg tablet strength |
|---|---|---|---|---|
| Bioequivalence Studies | ≧79.0 | ≧79.0 | ≧79.0 | ≧44.0 |

The term "bioequivalence," as used herein, means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. See Code of Federal Regulations, Title 21, Apr. 1, 1997 edition, Part 320.1, Definitions (e) Bioequialence, page 195, which is incorporated by reference herein in its entirety.

Table 7 also depicts the fit facor $F_2$ for thirteen (13) of the sixteen (16) over-the-counter SR niacin products referenced in Tables 5A and 5B compared to the dissolution curve of Niaspan®. As can be seen from the fit factor $F_2$ data in Table 7, the thirteen (13) over-the-counter SR niacin products are not bioequivalent to Niaspan®, in view of the fact that the fit factor $F_2$ is less than 79 for all such products.

TABLE 7

| Brand | Niaspan® K4061A-1 500 mg | GTRN 250 86A6014C 250 mg | Nicobid MN0928 500 mg | Goldline 12 12L51229 500 mg | Goldline 87 87L51081 500 mg | Goldline 89 89G5612C 500 mg | Rugby MO M070E 500 mg |
|---|---|---|---|---|---|---|---|
| F2 | 79 | 54.3 | 39.4 | 60.6 | 64.5 | 45.0 | 38.7 |

| Brand | Rugby 5L 5L01707 500 mg | Time Cap A051G 500 mg | Major 5F00753 500 mg | Upsher-Smith 16020 500 mg | Geneva 4B124 500 mg | Mason 501199 500 mg | Endurance 11504 500 mg |
|---|---|---|---|---|---|---|---|
| F2 | 57.3 | 53.9 | 48.7 | 56.3 | 39.3 | 60.8 | 59.6 |

The percent of the dose excreted in urine as niacin and NUA as well as the percent of the dose excreted in urine as metabolites other than niacin and NUA relative to the total dose recovered is due to saturable first-pass metabolism. Thus, because it is now discovered that the rate of niacin absorption determines the amount of drug that is excreted as niacin and NUA versus all other niacin metabolites, the rate of absorption can be used to control the amount of Pathway 1 and Pathway 2 metabolites produced. This can be depicted from urine collection data obtained following multiple-daily administrations of Niaspan® to healthy human volunteers, as illustrated in Table 8.

TABLE 8

| Metabolites recovered | 2 × 500 mg Niaspan® tablets | 2 × 750 mg Niaspan® tablets | 2 × 1000 mg Niaspan® tablets | 3 × 1000 mg Niaspan® tablets |
|---|---|---|---|---|
| Niacin + NUA | | | | |
| Mean | 12.2% | 21.3% | 32.4% | 41.9% |
| Range | 4.5–25.7% | 11.0–44.8% | 21.7–48.2% | 25.4–66.1% |
| All others | | | | |
| Mean | 87.8% | 78.7% | 67.6% | 58.1% |
| Range | 74.3–95.5% | 55.2–89.0% | 51.8–78.3% | 33.9–74.6% |

Table 8 reflects the range and mean of metabolites recovered in the urine from 27 individuals at 24 hours after administration of the respective Niaspan® tablet strengths once per day at night for 6 days. The numbers recited in Table 8 represent the mean and range for all 27 patients for each dosage regimen.

Turning now to FIG. 5, it depicts actual metabolite recovery data from two studies involving six subjects where the amount of Phase I pathway (Pathway 2) and Phase II pathway (Pathway I) metabolites excreted in urine at steady-state following the administration of IR (500 mg tid) and SR niacin (500 mg qid), which were quantified. FIG. 5 further depicts that SR niacin results in little Phase II pathway (Pathway 1) metabolites (niacin and nicotinuric acid) and that almost all of the niacin from the SR formulation was converted to Phase I pathway (Pathway 2) oxidative metabolites. Moreover, little to no flush was reported by the individuals who received the SR niacin product in this study, while nearly all subjects who received IR niacin experienced flush. Because all six subjects in this study who consumed the SR niacin product experienced elevations in liver enzymes at least 3 times greater than the upper limit of normal, the study was prematurely terminated. In the IR niacin study where much less Pathway 2 metabolites were produced, no subjects experienced elevations in liver enzymes. It is believed that, because the SR niacin products are designed with a slow dissolution or absorption rate which results in a situation where the rate of niacin presentation to the liver is so slow that Pathway 2 is never saturated and the major metabolites produced are Pathway 2 metabolites, hepatotoxicity will ensue from SR niacin products. On the other hand, when IR niacin is administered, it is believed that, because the presentation of niacin to the liver is so rapid that Pathway 2 is saturated almost immediately, the major metabolites produced are Pathway 1 metabolites and the patient experiences flush.

As compared to the IR and SR niacin formulations, the unique absorption rate of Niaspang is believed to result in a urine metabolite profile that balances the extremes of these two metabolic profiles. In other words, the unique absorption profile following Niaspan® administration balances the Pathway 1 and Pathway 2 metabolites thereby minimizing the risk of drug-induced hepatotoxicity at the expense of possibly causing some flush. To minimize the flush, the unique titration regimen recommended at the beginning of Niaspan® therapy is designed to allow the body to down regulate or desensitize itselffrom the prostaglandin effects (PGD$_2$) resulting from the administration of niacin. For those individuals who are initiating niacin therapy, it is possible to avoid significant flushing by starting with a unique Niaspan® titration pack. In accordance with the present invention, the novel titration packs include Niaspan® tablets in at least the following three dosage regimens, i.e., 375 mg, 500 mg and 750 mg, and are generally administered as follows: the new patient receives Niaspan® 375 mg Once-A-Night™ for seven days, followed by Niaspan® 500 mg Once-A-Night™ for seven days, and then Niaspan® 750 mg Once-A-Night™ for seven days, after which they may start receiving therapeutic doses of Niaspan® starting at 1000 mg Once-A-Night™ as two, 500 mg tablets.

Once titrated, it is important for the patients to take therapeutic doses of Niaspan® as directed in the labeling to avoid the risk of significant flushing early in the initial therapy and hepatotoxicity later in the therapy. That is, patients should take two, 500 mg Niaspan® tablets for a 1000 mg dose, two, 750 mg Niaspan® tablets for a 1500 mg dose and two, 1000 mg Niaspan® tablets for a 2000 mg dose. It is believed that early flushing and subsequent hepatotoxicity can be avoided by following such directions in view of the fact that the 375 mg and 500 mg Niaspan® tablets are not bioequivalent to the 750 mg and 1000 mg Niaspan® tablets, i.e., the 375 mg, 500 mg and 750 mg Niaspan® tablets release niacin at a slower rate than the Niaspan® 1000 mg tablets. Moreover, the 375 mg and 500 mg Niaspan® tablets are believed to release niacin at the slowest rate. Thus, and in accordance with the present invention, early in niacin therapy, when a patient is most susceptible to flush and taking low doses, the patient should receive the slower dissolving Niaspan® tablets to avoid quick saturation of Pathway 2 and to permit the body to desensitize itselffrom the prostaglandin effects (PDG$_2$) resulting elevated niacin concentrations, so that flush can be avoided. However, as the patient is titrated to higher doses (no more than about 500 mg increments at four-week intervals), the Niaspan® tablets used should release their niacin at faster rates to reduce the risk of hepatotoxicity. It is believed that, at this point, the patients prostaglandin system has acclimated itself to niacin and the risk of flush is minimized.

Other biopharmaceutic characteristics of the Niaspan® tablets include AUC, Cmax and Tmax By the term "AUC," it refers to the area under a plasma concentration curve of niacin or NUA ho and is based upon the rate and extent of absorption of niacin following ingestion of a certain dose of a niacin formulation. By the term "Cmax," as used herein, it is meant to refer to the peak or maximum concentration of niacin or NUA achieved in the plasma following ingestion of a certain dose of a niacin formulation. Cmax occurs generally at about the time when the niacin in the formulation has been almost completely absorbed therefromrl, and it too is based upon the rate and extent of absorption of niacin following ingestion of a certain dose of a niacin formulation. The term "Tmax" refers to the time that Cmax occurs following ingestion. The Tmax for the Niaspan® products of the present invention generally occurs between about 5.6 hours and about 6 hours following ingestion, which is believed to be due in part to the saturable first pass effect of the liver.

Turning now to Table 9, it depicts both AUC and Cmax data for niacin and NUA obtained from the administration of a single dose of Niaspan® at the dosage strengths identified therein to individuals from whom blood was withdrawn at frequent intervals over a 24 hour period following ingestion to detect the niacin and NUA concentrations from which the absorption rate of niacin can be determined. According to Table 9, the 375 mg Niaspan® tablets have a niacin Cmax of about 3.39 µg/ml and AUC of about 5.8 µghr/ml and an NUA Cmax of about 2.4 µg/ml and an AUC of about 9.6

µghr/ml. Table 9 further reports that the 500 mg Niaspan® tablets have a niacin Cmax in the range of from about 1.13 µg/ml to about 10.1 µg/ml with a mean of about 3.71 µg/ml and an AUC in the range of about 1.8 µghr/ml to about 33.7 µghr/ml with a mean of about 8.9 µghr/ml. Still further, Table 9 reports that the 500 mg Niaspan® tablets have an NUA Cmax in the range of about 1.62 µg/ml to about 3.4 µg/ml with a mean of about 2.18 µg/ml and an AUC in the range of about 5.5 µghr/ml to about 15.7 µghr/ml with a mean of about 8.7 µghr/ml.

Table 9 further reports that the 750 mg Niaspan® tablets have a niacin Cmax in the range of from about 7.68 µg/ml to about 9.11 µg/ml with a mean of about 8.40 µg/ml and an AUC in the range of about 21.1 µghr/ml to about 21.5 µghr/ml with a mean of about 21.3 µghr/ml. Still further, Table 9 reports that the 750 mg Niaspan® tablets have an NUA Cmax in the range of about 2.97 µg/ml to about 3.2 µg/ml with a mean of about 3.09 µg/ml and an AUC in the range of about 11.5 µghr/ml to about 12.7 µghr/ml with a mean of about 12.1 µghr/ml.

Table 9 further reports that the 1000 mg Niaspan® tablets have a niacin Cmax in the range of from about 9.29 µg/ml to about 16.6 µg/ml with a mean of about 12.54 µg/ml and an AUC in the range of about 24.2 µghr/ml to about 42.6 µghr/ml with a mean of about 33.2 µghr/ml. Still further, Table 9 reports that the 1000 mg Niaspan® tablets have an NUA Cmax in the range of about 2.81 µg/ml to about 4.45 µg/ml with a mean of about 3.55 µg/ml and an AUC in the range of about 12.0 µghr/ml to about 18.8 µghr/ml with a mean of about 15.4 µghr/ml.

TABLE 9

| Dose mg | Study | Tablet mg | Niacin Cmax ug/ml | Niacin AUC ughr/mL | NUA Cmax ug/ml | NUA AUC ughr/mL |
|---|---|---|---|---|---|---|
| 1500 | A | 375 | 3.39 | 5.8 | 2.4 | 9.6 |
| 1500 | B | 500 | 10.1 | 33.7 | 3.4 | 15.7 |
| 1500 | C | 500 | 5.76 | 15.7 | 2.33 | 10.1 |
| 1500 | C | 500 | 5.98 | 15.8 | 2.33 | 10.2 |
| 1500 | A | 500 | 3.04 | 5.8 | 2.25 | 9 |
| 1500 | D | 500 | 2.89 | 4.76 | 2.16 | 7.6 |
| 1500 | D | 500 | 3.14 | 5.1 | 2.31 | 8.6 |
| 1500 | D | 500 | 2.36 | 3.1 | 1.98 | 7.2 |
| 1500 | E | 500 | 1.81 | 3.1 | 1.89 | 7 |
| 1500 | E | 500 | 1.13 | 1.8 | 1.62 | 5.5 |
| 1500 | E | 500 | 1.69 | 2.2 | 1.8 | 6 |
| 2000 | F | 500 | 4.66 | 11.6 | 2.28 | 9.3 |
| 2000 | G | 500 | 2.02 | 4.6 | 2.06 | 9.0 |
| 1500 | H | 750 | 9.11 | 21.5 | 3.2 | 11.5 |
| 1500 | I | 750 | 7.68 | 21.1 | 3.2 | 11.5 |
| 2000 | G | 1000 | 11.6 | 31.4 | 3.35 | 14.3 |
| 2000 | G | 1000 | 9.39 | 24.2 | 2.91 | 12 |
| 2000 | J | 1000 | 15.8 | 42.6 | 4.21 | 18.4 |
| 2000 | J | 1000 | 16.6 | 41.4 | 4.45 | 18.8 |
| 2000 | K | 1000 | 9.29 | 26.2 | 2.81 | 13.3 |

Turning now to the Once-A-Night™ administration of Niaspan®, it is believed that a significant amount of lipid synthesis occurs at night. Thus, it is believed that the administration of Niaspan® in the evening or at bedtime produces niacin concentrations in the body at the optimal time necessary to interfere with the conversion of free fatty acids into LDL-cholesterol, thereby producing its beneficial effects. The Once-A-Night™ administration regimen is also believed to minimize the risk of hepatotoxicity as follows. Because SR niacin is generally administered at least twice daily and Niaspan® is administered once-daily at night, the SR niacin products will result in a greater accumulation of Pathway 2 metabolites because it is re-administered before sufficient metabolite has left the body. As a consequence, the Pathway 2 metabolites will pass over the toxic threshold causing drug-induced hepatotoxicity. On the other hand, Niaspan® produces less Pathway 2 metabolite and is administered less frequently allowing sufficient time for clearance of metabolites keeping their accumulation below the toxic threshold. Thus, it is believed that the unique combination of the controlled niacin absorption rate of Niaspan®, the adherence to the Niaspan® titration schedule and/or the Once-A-Night™ administration regimen are responsible for the efficacy of Niaspan® and the minimized flush and hepatotoxicity associated with its administration. In other words, it is believed that Niaspan's® unique absorption rate profile combined with its unique titration schedule and its unique Once-A-Night™ regimen are responsible for its lower incidence of flush relative to IR niacin, its minimal risk of drug-induced hepatotoxicity relative to SR niacin, and its efficacy in hyperlipidemia.

The present invention employs nicotinic acid or a compound other than nicotinic acid itself which the body metabolizes into nicotinic acid, thus producing the same effect as described herein. The other compounds specifically include, but are not limited to the following: nicotinyl alcohol tartrate, d-glucitol hexanicotinate, aluminum nicotinate, niceritrol and d, 1-alpha-tocopheryl nicotinate. Each such compound will be collectively referred to hereinbelow by "nicotinic acid."

As stated hereinabove, nicotinic acid has been employed in the past for the treatment of hyperlipidemia, which condition is characterized by the presence of excess fats such as cholesterol and triglycerides, in the blood stream. According to the present invention, an intermediate release composition of nicotinic acid is prepared as an example. As indicated herein, "intermediate release" is understood to mean a composition or formulation which, when orally administered to a patient to be treated, the active ingredient will be released for absorption into the blood stream over a period of time which is slower than that of IR niacin formulations, but faster and different than SR niacin products. For example, it is preferred that in a dosage of about 1000–3000 milligrams (herein "mg(s)") of nicotinic acid, approximately 100 percent of the nicotinic acid will be released to the blood stream in about 5 to about 9 hours.

The specific intermediate release composition according to the present invention employs an effective antihypertipidemic amount of nicotinic acid. By "effective anithyperlipidemic amount" it is understood to mean an amount which when orally administered to a patient to be treated, will have a beneficial effect upon the physiology of the patient, to include at least some lowering of total cholesterol, LDL cholesterol, triglycerides and Lp(a) and at least some increase in HDL cholesterol in the patient's blood stream. An exemplary effective antihyperlipidemic amount of nicotinic acid would be from about 250 mgs to about 3000 mgs of nicotinic acid to be administered according to the invention as will be more fully described hereinbelow. This amount will very dependent upon a number of variables, including the psychological needs of the patient to be treated.

Preferably, there is also included in the intermediate release composition according to the present invention, a swelling agent which is compounded with the nicotinic acid, such that when the composition is orally administered to the patient, the swelling agent will swell over time in the patient's gastrointestinal tract, and release the active nicotinic acid, or a compound which produces nicotinic acid into the gastrointestinal system for absorption into the blood stream, over a period of time. As is known in the art, such swelling agents and amounts thereof, may be preselected in order to control the time release of the active ingredient. Such swelling agents include, but are not limited to, polymers such as sodium carboxymethylcellulose and methylcellulose and waxes such as bees wax and natural materials such as gums or gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxypropyl methylcellulose, in an amount ranging from about 5% to about 50% parts by weight per 100 parts by weight of tablet or formulation. The preferred example will ensure a sustained time release over a period of approximately 5–9 hours as demonstrated by in vitro dissolution techniques known to the art.

A binder may also be employed in the present compositions. While any known binding material is useful in the present invention, it is preferred to employ a material such as one or more of a group of polymers having the repeating unit of 1-ethenyl-2-pyrrolidinone. These polymers generally have molecular weights of between about 10,000 and 700,000, and are also known as "povidone".

Amounts of the binder material will of course, vary depending upon the nature of the binder and the amount of other ingredients of the compositions. An exemplary amount of povidone in the present compositions would be from about 1% to about 5% by weight of povidone per 100 parts by weight of the total formulation.

Processing aids such as lubricants, including stearic acid, may also be employed, as is known in the art. An exemplary amount of stearic acid in the present compositions would be from about 0.5% to about 2.0% by weight per 100 parts by weight of table or formulation.

Examples ofvarious embodiments of the present invention will now be further illustrated with reference to the following examples.

General Experimental In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in Table IA hereinbelow.

TABLE IA

Test Tablet Composition

| Ingredient | 375 mg | 500 mg | 750 mg |
|---|---|---|---|
| Nicotinic Acid | 375.0 | 500.0 | 750.0 |
| Hydroxypropyl methylcellulose | 188.7 | 203.0 | 204.7 |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. More specifically, Niaspan® once-daily tablets in accordance with the present invention utilize a hydrophilic matrix controlled drug delivery system. This is a dynamic system composed of polymer wetting, polymer hydration and polymer disintegration/dissolution. The mechanism by which drug release is controlled depends on, for example, initial polymer wetting, expansion of the gel layer, tablet erosion and niacin solubility. After initial wetting, the hydrophilic polymer starts to partially hydrate, forming a gel layer. As water permeates into the tablet increasing thickness of the gel layer, drug diffuses out of the gel layer. As the outer layer of the tablet becomes fully hydrated it erodes. It is believed that this erosion results in additional drug release. The controlled release from this matrix delivery system can be modified depending on the type of molecular weight of hydrophilic polymer used.

A Niaspan® formulation consists of Niacin, Methocel® E10M Premium, Povidone K90 and Hystrene 5016 (stearic acid). Methocel® E10M Premium is utilized as a controlled-release agent in the Niaspan® fomulation. Methocel is a partly O-methylated and O-(2-hydroxypropylated) cellulose and is available in several grades which vary in terms of viscosity and degree of substitution. Methocel is manufactured by Dow Chemical.

Povidone K90 is employed as a granulating/binding agent in a Niaspan® formulation. Povidone is a synthetic polymer consisting of linear 1-vinyl-2-pyrrolidone groups, the degree of polymerization of which results in polymers of various molecular weights, or as indicated above. It is characterized by its viscosity in aqueous solution, relative to that of water, expressed as a K-value, ranging from 10–120. Povidone K90 has an approximate molecular weight of 1,000,000. Povidone is a hygroscopic, water soluble material. Povidone K90 presents in a Niaspan® formulation is manufactured by ISP (International Speciality Products). Hystrene 5016 is utilized as an external lubricant in theNiaspan® formulation. Hystrene 5016 is a mixture of stearic acid and palmitic acid. The content of stearic acid is not less than about 40.0% and the sum of the two acids is not less than about 90.0%. Hystrene 5016 is manufactured by Witco. Refer to Table IB for Niaspan® formulation details.

Qualitatively, the four tablet strength formulations are identical. The major component of each formulation is a granulated mixture of Niacin, Methocel E10M and Povidone K90. The granulation process improves compression properties.

TABLE IB

Niaspan ® Tablet Formulations

| Niaspan ® Product | 375 mg Tablets | 500 mg Tablets | 750 mg Tablets | 1000 mg Tablets |
|---|---|---|---|---|
| Formulation, % Tablet | | | | |
| Niacin | 64.4 | 70.5 | 77.4 | 83.1 |
| Methocel E10M Premium (Intragranular) | 7.4 | 8.1 | 8.9 | 9.5 |
| Povidone K90 | 2.2 | 2.4 | 2.7 | 2.9 |
| Methocel E10M Premium (Extragranular) | 25.0 | 18.0 | 10.0 | 3.5 |
| Hystrene 5016 (Stearic Acid) | 1.0 | 1.0 | 1.0 | 1.0 |
| Tablet weight, mg | 582.5 | 709.5 | 968.6 | 1203.6 |

Niaspan® formulations are presented in white caplet shape tablets. Caplet dimensions differ with respect to product strength. The 375 mg and 500 mg Niaspan® tablets are compressed with tooling measuring approximately 0.687" in length×0.281∴ by width. The length and width of the 750 mg and 1000 mg tooling measures approximately 0.750"×0.320". Target tablet weight and hardness dictate thickness across the four Niaspan® products. The production of the Niaspan® tablets will now be described generally as set forth below.

| Niaspan ® Granulation Process Flow Chart | | |
| --- | --- | --- |
| Raw Materials | Process Flow | Equipment |
| Niacin<br>Povidone K90<br>Methocel E10M<br>(Intragranular)<br>Purified Water | Granulate<br>↕<br>Dry<br>↕<br>Parcel size reduction | High shear granulator<br>(Littleford FM130)<br><br>Fluid bed drier<br>(Gladd fluid bed drier)<br><br>Mill<br>(Kemutec Betagrind) |

Niaspan® Granulation Process Description

Naspan® granulation raw materials are dispensed and granulated in a high shear granulator. The wet granules are sieved into a fluid bed drier and dried. When the drying process is complete, the granules are milled. Milling ensures uniform particle size distribution throughout the Niaspan® granulation.

Niaspan® Tablet Process Flow Chart

| Niaspan ® Tablet Process Flow Chart | | |
| --- | --- | --- |
| Raw Materials | Process Flow | Equipment |
| | Niaspan ® Tablet Blend | |
| Methocel E10M<br>(Extragranular)<br>Hystrene 5016<br>(Stearic acid) | Blend Milled<br>Niaspan ® granules<br>with extragranular<br>Methocel E10M<br>and Hystrene 5016<br>↕<br>Niaspan ® Table Manufacture<br><br>Compress Niaspan ®<br>Tablet Blend | Blender<br>(Patterson-Kelley<br>V-Blender)<br><br><br><br><br><br>Rotary tablet press |

Niaspan® Tablet Process Description

A Niaspan® tablet blend is manufactured by blending the Niaspan® granulation, extragranular Methocel E10M and Hystrene 5016. The quantities of each Niaspan® tablet blend component will depend on the particular Niaspan® dose being manufactured (refer to Table IB). A Niaspan® tablet blend is compressed to form Niaspan® tablets. Niaspan® tablet physical properties will vary depending on the particular Niaspan® dose being manufactured.

Production of Niaspan® tablets will now be discussed in greater detail. The initial stage of manufacturing is the same for all four tablet strengths of Niaspan® (375, 500, 750 and 1000 mg). One batch of Niaspan® granulation is comprised of four individual 40.0 kg unites of granulation which are processed separately, but under like conditions. The four individual granulations are sampled and tested individually and subsequently released for blending. The base granulation is not strength specific and may be used to manufacture any tablet strength of Niaspan®.

The ingredients in the base granulation are set froth in Table IC below:

TABLE IC

| Component | Function | Quantity per kilogram granulation (kg) | % per kilogram granulation (%) | Quantity per 160.0 kg batch (kg) |
| --- | --- | --- | --- | --- |
| Niacin, USP | Drug Substance | 0.87 | 87.00 | 139.20 |
| Povidine, UPS | Binder | 0.03 | 3.00 | 4.80 |

TABLE IC-continued

| Component | Function | Quantity per kilogram granulation (kg) | % per kilogram granulation (%) | Quantity per 160.0 kg batch (kg) |
| --- | --- | --- | --- | --- |
| Methocel USP, E10M Premium CR Grade | Controlled-Release Agent | 0.10 | 10.00 | 16.00 |
| Purified Water, USP* | Granulation Reagent | 0.00* | 0.00* | 48.0 |
| Total | | | | 160.00 |

*Purified Water, USP is used as granulation reagent and does not appear in the finished granulation.

Raw materials are quantatively dispensed into appropriately labeled double polyethylene-lined containers using calibrated scales. Purified Water, USP is dispensed into an appropriate vessel from which it is later pumped during the wet-massing operation.

A Littleford FM130 granulator is charged with approximately one half of the Niacin, USP required for the process unit (~17.4 kg) followed by about 4.00 kg of Methocel, USP E10M Premium CR Grade; about 1.20 kg of Povidine, USP; and the balance of the Niacin, SP (~17.40 kg). The powder bed is dry mixed in the Littleford FM130 granulator, with choppers on, for approximately 1 minute. At the completion of the 1-minute pre-mix cycle, about 12.0±0.05 kg of Purified Water, USP are sprayed onto the powder bed at a rate of about 2.40±0.24 kg/minute. Immediately following the addition of the Purified Water, USP, the unit is granulated for about 5 minutes.

The granulated unit is discharged into double polyethylene-lined containers and then manually loaded into a Glatt bowl while being passed through a #4 mesh screen. The Glatt bowl is loaded into a Glatt TFO-60 fluid-bed drier with an inlet air temperature setting of about 70° C.±5° C. The unit is dried until a moisture level of ≤1.0% is obtained as determined using a Computrac® Moisture Analyzer, model MA5A. The dried granulation is discharged into appropriately labeled, double polyethylene-lined drums and reconciled.

The dried and reconciled granulation is passed through a Kemutec BetaGrind mill equipped with a 1.5 mm screen and running at approximately 1500 RPM. The milled granulation is collected into appropriately labeled, double polyethylene-lined drums and reconciled. The milled granulation is sampled and tested by Quality Control and released prior to further processing.

The released granulation units are charged to a Patterson-Kelley 20 ft3 V-blender after which they are blended together for about 10±1 minutes and then discharged to appropriately labeled, double polyethylene-lined containers.

As stated above, Niaspan® tablets are formulated from a common granulation which is blended with appropriate quantities of Methocel, USP E10M Premium CR Grade and Stearic Acid, NF to achieve the final dosage formulation. Tables IA and IB describe the formulation for each Niaspan® tablet strength, 375 mg, 500 mg, 750 mg and 1000 mg, respectively.

Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regiment of the above discussed tablets, totaling approximately 1500 mg of nicotinic acid, once per day before going to bed. After eight weeks of this regimen, the patients were again tested for lipid profiles. The results of tests conducted at eight w weeks, showing the changes in the lipid profiles as a percentage change from the baseline, are reported in the table hereinbelow. Positive numbers reflect percentage increases and negative numbers reflect percentage decreases in this table.

TABLE II

Patient Study Lipid Profile Data

| Pt. No. | Total-C | LDL-C | Apo B | Trigs | HDL-C | HDL-C | Lp(a) |
|---|---|---|---|---|---|---|---|
| GROUP A | | | | | | | |
| 1 | −8.2 | −12.0 | NA | −17.3 | 22.0 | NA | NA |
| 2 | −5.9 | −27.0 | NA | −28.7 | 65.0 | NA | NA |
| 3 | −15.1 | −13.0 | NA | −22.0 | −9.1 | NA | NA |
| 4 | −3.3 | −10.0 | NA | 61.6 | 3.8 | NA | NA |
| 5 | −16.5 | −17.7 | NA | −28.8 | 11.1 | NA | NA |
| 6 | −12. | −25.9 | NA | −42.0 | 51.6 | NA | NA |
| 7 | −24.2 | −31.4 | NA | −30.4 | 12.5 | NA | NA |
| 8 | −6.7 | −7.4 | NA | −42.4 | 18.8 | NA | NA |
| 9 | 4.5 | 1.1 | NA | 7.2 | 9.2 | NA | NA |
| 10 | 2.8 | −0.2 | NA | −2.7 | 22.9 | NA | NA |
| 11 | −13.0 | −9.4 | NA | −54.0 | 44.3 | NA | NA |
| Mean | −8.9 | −9.4 | NA | −18.9 | 23.0 | NA | NA |
| p-Value | 0.0004 −8.9 | 0.0001−13.9 | | 0.0371 | 0.0068 | | |
| GROUP B | | | | | | | |
| 1 | −19.2 | −27.1 | −24.4 | −33.4 | 20.0 | 22.3 | −81.9 |
| 2 | −32.2 | −35.7 | −28.0 | −60.4 | 4.3 | 3.2 | −25.3 |
| 3 | −21.4 | −33.6 | −35.6 | −33.4 | 30.4 | 38.6 | −17.4 |
| 4 | −19.9 | −24.6 | −15.1 | −20.8 | 9.6 | 16.1 | −27.0 |
| 5 | −3.3 | −2.1 | −29.4 | −41.1 | 5.8 | 2.4 | −22.4 |
| 6 | | | PATIENT WITHDREW FROM STUDY | | | | |
| 7 | 23.1 | −32.6 | −42.6 | −58.6 | 49.2 | 68.9 | −14.3 |
| 8 | 24.8 | 34.0 | −28.4 | 5.5 | 6.5 | −6.8 | Na |
| 9 | 10.1 | 12.0 | −16.8 | −11.6 | 2.7 | −12.3 | 40.6 |
| 10 | −2.9 | −7.7 | −28.0 | −59.0 | 53.1 | 70.5 | −41.2 |
| 11 | −10.5 | −18.8 | −25.3 | −53.4 | 31.8 | 39.7 | NA |
| 12 | −20.0 | −30.8 | −30.4 | 11.7 | 21.1 | 25.0 | −28.4 |
| 13 | 17.4 | 16.8 | −17.5 | −17.5 | 51.3 | 51.9 | 38.5 |
| 14 | −9.4 | −16.6 | −32.0 | −46.9 | 52.3 | 67.6 | 17.6 |
| MEAN | −8.7 | −12.8 | −32.2 | −27.2 | 25.3 | 30.1 | −17.9 |
| p-Value | 0.0002 | <0.0001 | 0.0001 | <0.001 | <0.0001 | 0.0002 | <0.0199 |
| Combined | −8.7 | −13.3 | Gp B | −26.1 | 25.3 | Gp B | Gp B |
| p-Value | 0.0002 | <0.0001 | only | <.0001 | <0.0001 | only | only |

The data reported in Table II shows that the LDL levels in the Group A patients had a mean decrease of −13.9% and triglyceride decrease of −18.9% HDL cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reduction when compared to sustained release formulations dosed during daytime hours on a milligram per milligram basis. Additionally, the increases in HDL cholesterol obtained from doing the sustained release formulation during the evening or at night were ±23.0% for one group and +25.3% for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES III–VII hereinbelow.

TABLE III

THE EFFECT OF NIASPAN ® THERAPY
ON AST (SGOT) LEVELS (U/L)
(1500 mgs dosed once-a-day at night)
(n = 28)

| | | Weeks of Therapy With Niaspan ® | | | Reference |
|---|---|---|---|---|---|
| Pt # | Baseline | 2 Wks. | 4 Wks. | 8 Wks. | Range |
| | | GROUP A | | | |
| 1 | 28 | 29 | 25 | 24 | 0–50 |
| 2 | 24 | 25 | 24 | 26 | 0–50 |
| 3 | 17 | 18 | 22 | 21 | 0–50 |
| 4 | 14 | 16 | 15 | 17 | 0–50 |
| 5 | 22 | NA | 32 | 52 | 0–50 |
| 6 | 21 | 17 | 17 | 14 | 0–50 |
| 7 | 17 | 17 | 14 | 18 | 0–50 |
| 8 | 20 | 21 | 22 | 22 | 0–50 |
| 9 | 16 | 16 | 17 | 20 | 0–50 |
| 10 | 18 | 21 | 21 | 25 | 0–50 |
| 11 | 21 | 21 | 22 | 21 | 0–50 |

TABLE III-continued

THE EFFECT OF NIASPAN ® THERAPY
ON AST (SGOT) LEVELS (U/L)
(1500 mgs dosed once-a-day at night)
(n = 28)

| Pt # | Baseline | Weeks of Therapy With Niaspan ® 2 Wks. | 4 Wks. | 8 Wks. | Reference Range |
|---|---|---|---|---|---|
| | | GROUP B | | | |
| 1 | 23 | 25 | 38 | 33 | 0–50 |
| 2 | 20 | 20 | 21 | 21 | 0–50 |
| 3 | 15 | 20 | 18 | 19 | 0–50 |
| 4 | 28 | 22 | 28 | 26 | 0–52 |
| 5 | 23 | 21 | 17 | 18 | 0–50 |
| 6 | PATIENT WITHDREW DUE TO FLUSHING | | | | |
| 7 | 21 | 18 | 18 | 19 | 0–50 |
| 8 | 18 | 19 | 18 | 19 | 0–50 |
| 9 | 15 | 16 | 18 | 15 | 0–50 |
| 10 | 16 | 15 | 19 | 28 | 0–50 |
| 11 | 20 | 22 | 24 | 28 | 0–50 |
| 12 | 23 | 25 | 28 | 22 | 0–50 |
| 13 | 20 | 15 | 20 | 19 | 0–50 |
| 14 | 18 | 25 | 20 | 18 | 0–50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ® THERAPY
ON ALT (SGPT) LEVELS (U/L)
(1500 mgs dosed once-a-day at night)
(n = 28)

| Pt # | Baseline | Weeks of Therapy With Niaspan ® 2 Wks. | 4 Wks. | 8 Wks. | Reference Range |
|---|---|---|---|---|---|
| | | GROUP A | | | |
| 1 | 32 | 28 | 39 | 30 | 0–55 |
| 2 | 24 | 25 | 23 | 26 | 0–55 |
| 3 | 18 | 23 | 30 | 30 | 0–55 |
| 4 | 7 | 13 | 14 | 14 | 0–55 |
| 5 | 14 | NA | 43 | 46 | 0–55 |
| 6 | 22 | 11 | 14 | 10 | 0–55 |
| 7 | 9 | 7 | 11 | 7 | 0–55 |
| 8 | 16 | 18 | 23 | 21 | 0–55 |
| 9 | 14 | 17 | 20 | 14 | 0–55 |
| 10 | 14 | 15 | 17 | 19 | 0–55 |
| 11 | 18 | 18 | 20 | 16 | 0–55 |
| | | GROUP B | | | |
| 1 | 16 | 17 | 27 | 29 | 0–55 |
| 2 | 16 | 14 | 15 | 22 | 0–55 |
| 3 | 13 | 21 | 13 | 16 | 0–55 |
| 4 | 23 | 20 | 26 | 17 | 0–55 |
| 5 | 21 | 23 | 17 | 15 | 0–55 |
| 6 | PATIENT WITHDREW DUE TO FLUSHING | | | | |
| 7 | 21 | 16 | 18 | 21 | 0–55 |
| 8 | 18 | 20 | 17 | 18 | 0–55 |
| 9 | 11 | 5 | 11 | 8 | 0–55 |
| 10 | 8 | 10 | 14 | 17 | 0–55 |
| 11 | 17 | 12 | 18 | 16 | 0–55 |
| 12 | 14 | 18 | 20 | 16 | 0–55 |
| 13 | 14 | NA | 11 | 10 | 0–55 |
| 14 | 23 | 23 | 19 | 19 | 0–55 |

TABLE IV-continued

THE EFFECT OF NIASPAN ® THERAPY
ON ALT (SGPT) LEVELS (U/L)
(1500 mgs dosed once-a-day at night)
(n = 28)

| Pt # | Baseline | Weeks of Therapy With Niaspan ® 2 Wks. | 4 Wks. | 8 Wks. | Reference Range |
|---|---|---|---|---|---|
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN ® THERAPY
ON ALKALINE PHOSPHATASE LEVELS (U/L)
(1500 mgs dosed once-a-day at night)
(n = 28)
Weeks of Therapy With Niaspan ®

| Pt # | Baseline | 2 Wks | 4 Wks | 8 Wks | Reference Range |
|---|---|---|---|---|---|
| GROUP A | | | | | |
| 1 | 52 | 56 | 57 | 55 | 20–140 |
| 2 | 103 | 100 | 89 | 102 | 20–140 |
| 3 | 54 | 45 | 53 | 51 | 20–140 |
| 4 | 70 | 68 | 71 | 91 | 20–140 |
| 5 | 77 | NA | 74 | 81 | 20–140 |
| 6 | 55 | 48 | 49 | 51 | 20–140 |
| 7 | 72 | 71 | 79 | 75 | 20–140 |
| 8 | 55 | 49 | 47 | 50 | 20–140 |
| 9 | 53 | 55 | 56 | 45 | 20–140 |
| 10 | 74 | 73 | 75 | 75 | 20–140 |
| 11 | 18 | 18 | 20 | 16 | 20–140 |
| GROUP B | | | | | |
| 1 | 73 | 67 | 89 | 95 | 20–140 |
| 2 | 82 | 64 | 72 | 71 | 20–140 |
| 3 | 73 | 69 | 81 | 82 | 20–140 |
| 4 | 37 | 36 | 37 | 38 | 20–140 |
| 5 | 65 | 53 | 54 | 61 | 20–140 |
| 6 | PATIENT WITHDREW DUE TO FLUSHING | | | | |
| 7 | 64 | 58 | 58 | 58 | 20–140 |
| 8 | 79 | 78 | 65 | 73 | 20–140 |
| 9 | 94 | 92 | 103 | 93 | 20–140 |
| 10 | 69 | 67 | 70 | 65 | 20–140 |
| 11 | 59 | 67 | 63 | 72 | 20–140 |
| 12 | 65 | 59 | 59 | 63 | 20–140 |
| 13 | 64 | 68 | 66 | 64 | 20–140 |
| 14 | 72 | 61 | 59 | 64 | 20–140 |

TABLE V-continued

THE EFFECT OF NIASPAN ® THERAPY
ON ALKALINE PHOSPHATASE LEVELS (U/L)
(1500 mgs dosed once-a-day at night)
(n = 28)
Weeks of Therapy With Niaspan ®

| Pt # | Baseline | 2 Wks | 4 Wks | 8 Wks | Reference Range |
|---|---|---|---|---|---|
| Combined Mean | 66.5 | 61.5 | 63.3 | 65.8 | |
| Change From Baseline | | −6.1% | −3.4% | +0.005% | |

Level of Significance: p = 0.0236

TABLE VI

THE EFFECT OF NIASPAN ® THERAPY
ON URIC ACID LEVELS (mg/dL)
(1500 mgs dosed once-a-day at night)
(n = 28)
Weeks of Therapy With Niaspan ®

| Pt # | Baseline | 2 Wks. | 4 Wks. | 8 Wks. | Reference Range |
|---|---|---|---|---|---|
| GROUP A | | | | | |
| 1 | 5.2 | 5.0 | 4.8 | 4.3 | 4.0–8.5 |
| 2 | 4.0 | 4.6 | 4.5 | 6.2 | 2.5–7.5 |
| 3 | 6.3 | 7.0 | 6.5 | 6.2 | 4.0–8.5 |
| 4 | 3.1 | 4.6 | 4.2 | 3.8 | 2.5–7.5 |
| 5 | 3.4 | NA | 3.3 | 4.2 | 2.5–7.5 |
| 6 | 6.6 | 5.5 | 5.6 | 4.7 | 4.0–8.5 |
| 7 | 3.8 | 4.5 | 4.3 | 4.9 | 2.5–7.5 |
| 8 | 4.4 | 3.8 | 5.1 | 4.5 | 2.5–7.5 |
| 9 | 3.9 | 4.5 | 4.6 | 3.5 | 2.5–7.5 |
| 10 | 2.6 | 2.9 | 2.8 | 2.7 | 2.5–7.5 |
| 11 | 4.7 | 5.5 | 5.2 | 5.3 | 2.5–7.5 |
| GROUP B | | | | | |
| 1 | 3.7 | 4.2 | 4.7 | 3.5 | 2.5–7.5 |
| 2 | 2.8 | 3.5 | 3.6 | 2.3 | 4.0–8.5 |
| 3 | 4.2 | 5.3 | 5.5 | 5.3 | 2.5–7.5 |
| 4 | 4.7 | 3.9 | 5.1 | 3.6 | 4.0–8.5 |
| 5 | 3.7 | 4.1 | 4.1 | 3.8 | 2.5–7.5 |
| 6 | PATIENT WITHDREW DUE TO FLUSHING | | | | |
| 7 | 5.8 | 6.6 | 6.6 | 6.8 | 2.5–7.5 |
| 8 | 4.7 | 4.3 | 5.4 | 5.6 | 2.5–7.5 |
| 9 | 3.7 | 4.6 | 5.1 | 3.8 | 2.5–7.5 |
| 10 | 4.2 | 5.0 | 4.4 | 8.5 | 2.5–7.5 |
| 11 | 1.9 | 3.0 | 2.8 | 5.0 | 2.5–4.5 |
| 12 | 5.6 | 5.4 | 6.2 | 5.6 | 4.0–8.5 |
| 13 | 4.2 | 4.6 | 4.6 | 5.3 | 2.5–7.5 |
| 14 | 5.5 | 5.4 | 6.1 | 5.3 | 2.5–7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN ® THERAPY
ON FASTING GLUCOSE LEVELS (mg/dL)
(n = 28)
Weeks of Therapy With Niaspan ®

| Pt # | Baseline | 2 Wks. | 4 Wks. | 8 Wks. | Reference Range |
|---|---|---|---|---|---|
| GROUP A | | | | | |
| 1 | 114 | 122 | 123 | 110 | 70–115 |
| 2 | 101 | 105 | 107 | 101 | 80–125 |
| 3 | 99 | 98 | 103 | 103 | 70–115 |
| 4 | 100 | 118 | 94 | 94 | 80–12580–12 |
| 5 | 89 | NA | 82 | 103 | 80–125 |
| 6 | 97 | 103 | 94 | 107 | 70–115 |
| 7 | 85 | 107 | 100 | 94 | 80–125 |
| 8 | 98 | 107 | 103 | 101 | 80–125 |
| 9 | 97 | 97 | 100 | 110 | 80–125 |
| 10 | 94 | 101 | 111 | 97 | 70–115 |
| 11 | 102 | 103 | 95 | 95 | 80–125 |
| GROUP B | | | | | |
| 1 | 101 | 97 | 83 | 99 | 70–115 |
| 2 | 90 | 95 | 96 | 89 | 80–125 |
| 3 | 96 | 98 | 95 | 97 | 70–115 |
| 4 | 116 | 139 | 113 | 125 | 80–125 |
| 5 | 88 | 98 | 91 | 95 | 70–115 |
| 6 | PATIENT WITHDREW DUE TO FLUSHING | | | | |
| 7 | 106 | 114 | 118 | 117 | 70–115 |
| 8 | 95 | 106 | 106 | 108 | 70–115 |
| 9 | 81 | 92 | 84 | 92 | 70–115 |
| 10 | 108 | 117 | 122 | 105 | 70–115 |
| 11 | 85 | 106 | 106 | 108 | 70–115 |
| 12 | 92 | 89 | 101 | 86 | 80–125 |
| 13 | 99 | 105 | 94 | 100 | 70–125 |
| 14 | 100 | 108 | 84 | 107 | 70–125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | \multicolumn{7}{c}{DOSE} | |
|---|---|---|---|---|---|---|---|---|
| | 0 | 500 | 1000 | 1500 | 2000 | 2500 | 3000 | TOTAL |
| McKenney Sr[b] Niacin[a] | | | | | | | | |
| AST | 23.8 | 27.9 | 40.4 | 36.6 | 56.5 | NA | 97.0 | |
| % | — | 117 | 170 | 154 | 237 | NA | 408 | |
| Invention Dosage[c] | | | | | | | | |
| AST | 24.3 | NA | 23.7 | 17.5 | 26.6 | 27.6 | 27.8 | |
| % | — | NA | 98 | 11398 | 109113 | 114 | 114 | |
| McKenney SR Niacin | | | | | | | | |
| ALT | 25.6 | 29.5 | 36.3 | 39.0 | 59.1 | NA | 100.0 | |
| % | — | 115 | 142 | 152 | 231 | NA | 391 | |
| Invention Dosage | | | | | | | | |
| ALT | 21.4 | NA | 18.7 | 22.6 | 21.3 | 22.4 | 21.8 | |
| % | — | NA | 87 | 106 | 100 | 105 | 102 | |
| McKenney SR Niacin | | | | | | | | |
| ALK | 95 | 95 | 106 | 105 | 136 | NA | 135 | |
| % | — | 100 | 112 | 111 | 143 | NA | 142 | |
| Invention Dosage | | | | | | | | |
| ALK | 74.7 | NA | 73.9 | 76.1 | 73.4 | 76.7 | 78.0 | |
| % | — | NA | 99 | 102 | 98 | 103 | 104 | |
| McKenney SR Niacin | | | | | | | | |
| Drop | — | 0 | 2 | 2 | 7 | NA | 7 | 18 |
| n | — | — | — | — | — | — | — | 23 |
| % | — | 0 | 9 | 9 | 30 | NA | 30 | 78 |
| Invention Dosage | | | | | | | | |
| Drop | — | — | 0 | 0 | 0 | 0 | 0 | 0 |
| n | — | — | 26 | 67 | 97 | 35 | 15 | 240 |
| % | — | — | 0 | 0 | 0 | 0 | 0 | 0 |
| 1 year | — | — | 15 | 46 | 77 | 31 | 15 | 184 |
| 1 year | — | — | 58 | 69 | 79 | 89 | 100 | 77 |

[a]Dosed twice-per-day as described in "A Comparison of the Efficacy and Toxic Effects of Sustained - vs Immediate - Release Niacin in Hypercholesterolemic Patients" by McKenney et al. Journal of the American Medical Association, March 2, 1994; Vol. 271, No. 9, pages 672–677.
[b]SR is "sustained release"
[c]Dosed once-per-day at night The results of the comparison of the studies reported in Table VIII show that the control group (the McKenney group) had 18 of 23, or 78 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The test results reported above indicate that this sustained release dosage form caused no elevation in liver function tests (i.e., no liver damage), no elevations in uric acid and only a small, 7.5% increase in fasting glucose levels which in fact decreased during continued therapy.

Thus it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations in liver function tests, uric acid or glucose levels for the hyperlipidemics.

Based upon the foregoing disclosure, it should now be apparent that the use of the compositions and methods described herein will carry out the objects set forth hereinabove. It is, therefore, to be understood that any variations in sustained release formulation evident fall within the scope of the claimed invention and thus, the selection of specific component elements can be determined without departing from the spirit of the invention herein disclosed and described. In particular, sustained release excipients, binders and processing aids according to the present invention are not necessarily limited to those exemplified hereinabove. Thus, the scope of the invention shall include all modifications and variations that may fall within the scope of the attached claims.

We claim:

1. An intermediate release nicotinic acid formulation suitable for oral administration once-a-day for treating hyperlipidemia without causing drug-induced hepatotoixicity to a level which woud require use of said intermediate release nicotinic acid formulation to be discontinued, said intermediate release nicotinic acid formulation containing at least about 375 mg of nicotinic acid and having:
   a nicotinic acid Cmax of about 3 μg/ml;
   a nicotinic acid Tmax in the range of between about 5.6 hours and about 6 bours; and
   an AUC for nictoinic acid of about 6 μghr/ml.

2. An intermediate release nicotinic acid formulation of claim 1, wherein said nicotinic acid formulation is a tablet.

3. An intermediate release nicotinic acid formulation suitable for oral administration once-a-day for treating hyperlipidemia without causing drug-induced hepatotoxicity to a level which would require use of said intermediate realse nicotinic acid formulation to be discontinued, said intermediate release nicotinic acid formulation containing at least about 375 mg of nicotinic acid and having:
  a nicotinuric acid Cmax of about 2 µg/ml;
  a nicotinuric acid Tmax in the range of between about 5.6 hours and about 6 hours; and
  an AUC for nictoinuric acid of about 10 µghr/ml.

4. An intermediate release nicotinic acid formulation of claim 3, wherein said nicotinic acid formulation is a tablet.

5. An intermediate release nicotinic acid formulation suitable for oral administration once-a-day for treating hyperlipidemia without causing drug-induced hepatotoxicity to a level which would require use of said intermediate release nicotinc acid fomlation to be discontinued, said intermediate release nicotinic acid formulation containing at least about 500 mg of nicotinic acid and having:
  a nicotinic acid Cmax in the range of from between about 1 µg/ml and 10 µg/ml;
  a nicotinic acid Tmax in the range of between about 5.6 hours and about 6 hours; and
  an AUC for nictoinic acid in the range of from between about 2 µghr/ml and about 34 µghr/ml.

6. An intermediate release nicotnic acid formulation of claim 5, wherein the Cmax has a mean of about 4 µg/ml and the AUC has a mean of about 9 µghr/ml.

7. An intermediate release nicotinic acid formulation of claim 5, wherein said nicotinic acid formulation is a tablet.

8. An intermediate release nicotinic acid formulation of claim 6, wherein said nicotinic acid formulation is a tablet.

9. An intermediate release nicotinic acid formulation suitable for oral admministration once-a-day for treating hyperlipidemia without causing drug-induced hepatotoxicity to a level which would require use of said intermediate release nicotinic acid formulation to be discontinued, said intermediate release nicotinic acid formulation containig at least about 500 mg of nicotinic acid and having:
  a nicotinuric acid Cmax in the range of from between about 2 µg/ml and 3 µg/ml;
  a nicotinuric acid Tmax in the range of beween about 5.6 hours and about 6 hours; and
  an AUC for nicotinuric acid in the range of from between about 6 µghr/ml and about 16 µghr/ml.

10. An intermediate release nicotinic acid formulation of claim 9, wherein the Cmax has a mean of about 2 µg/ml and the AUC has a mean of about 9 µghr/ml.

11. An intermediate release nicotinic acid formulation of claim 9, wherein said nicotinic acid formulation is a tablet.

12. An intermediate release nicotinic acid formulation of claim 10, wherein said nicotnic acid formulation is a tablet.

13. An intermediate release nicotinic acid formulation suitable for oral asministration once-a-day for treating hyperlipidemia without causing drug-induced hepatotoxcity to a level which would require use of said intermediate release nicotinic acid formlation to be discontinued, said intermediate release nicotinic acid formulation containing at least about 750 mg of nicotinic acid and having:
  a nicotinic acid Cmax in the range of from between about 8 µg/ml and 9 µg/ml;
  a nicotinic acid Tmax in the range of between about 5.6 hours and about 6 hours; and
  an AUC for nictoinic acid in the range of from between about 21 µghr/ml and about 22 µghr/ml.

14. An intermediate release nicotinic acid formulation of claim 13, wherein the Cmax has a mean of about 8 µg/ml and the AUC has a mean of about 21 µghr/ml.

15. An intermediate release nicotinic acid formulation of claim 13, wherein said nicotinic acid formulation is a tablet.

16. An intermediate release nicotinic acid formulation of claim 14, wherein said nicotinic acid formulation is a tablet.

17. An intermediate release nicotinic acid formulation suitable for oral administration once-a-day for treating hyperlipidemia without causing drug-induced hepatotoxicity to a level which would require use of said intermediate release nicotinic acid formulation to be discontinued, said intermediate release nicotinic acid formulation containing at least about 750 mg of nicotinic acid and having:
  a nicotinuric acid Cmax in the range of from between about 3 µg/ml and 3.2 µg/ml;
  a nicotinuric acid Tmax in the range of between about 5.6 hours and about 6 hours; and
  an AUC for nicotinuric acid in the range of from between about 11 µghr/ml and about 13 µghr/ml.

18. An intermediate release nocotinic acid formulation of claim 17, wherein the Cmax has a mean of about 3 µg/ml and the AUC his a mean of about 12 µghr/ml.

19. An intermediate release nicotinic acid formulation of claim 17, wherein said nicotinic acid formulation is a tablet.

20. An intermediate release nicotinic acid formulation of claim 19, wherein said nicotinic acid formulation is a tablet.

21. An intermediate release nicotrinic acid formulation suitable for oral administration once-a-day for treating hyperlipidemia without causing drug-induced hepatotoxicity to a level which would require use of said intermediate release nicotinic acid formulation to be discontinued, said intermediate release nicotinic acid formulation containg at least about 100 mg of nicoinic acid and having:
  a nicotinic acid Cmax in the range of from between about 9 µg/ml and 17 µg/ml;
  a nicotinic acid Tmax in the range of between about 5.6 hours and bout 6 hours; and
  an AUC for nictoinic acid in the range of from between about 24 µghr/ml and about 43 µghr/ml.

22. An intermediate release nicotinic acid formulation of claim 21, wherein the Cmax has a mean of about 13 µg/ml and the AUC has a mean of about 33 µghr/ml.

23. An intermediate release nicotinic acid formulation of claim 21, wherein said nicotinic acid formulation is a tablet.

24. An intermediate release nicotinic acid formulation of claim 22, wherein said nicotinic acid formuation is a tablet.

25. An intermediate release nicotinic acid formulation suitable for oral administration once-a-day for treating hyperlipidemia without causing drug-induced hepatotoxicity to a level which would require use of said intermediate release nicotinic acid formulation to be discontinued, said intermediate release nicotinic acid formulation containing at least about 1000 mg of nicotinic acid and having:
  a nicotinuric acid Cmax in the range of from between about 3 µg/ml and 5 µg/ml;
  a nicotinuric acid Tmax in the range of between about 5.6 hours and about 6 hours; and
  an AUC for niotinuric acid in the range of from between about 12 µghr/ml and about 19 µghr/ml.

26. An intermediate release nicotinic acid formulation of claim 25, wherein the Cmax has a mean of about 4 µg/ml and the AUC has a mean of about 15 µghr/ml.

27. An intermediate release nicotinic acid formulation of claim 25, wherein said nicotinic acid formulation is a tablet.

28. An intermediate release nicotinic acid formulation of claim 26, wherein said nicotinic acid formulation is a tablet.

* * * * *

UNITED STATES PATENT AND TRADEMARK OFFICE
CERTIFICATE OF CORRECTION

PATENT NO.        : 6,818,229 B1
APPLICATION NO.   : 08/962027
DATED             : November 16, 2004
INVENTOR(S)       : Eugenio A. Cefali et al.

Page 1 of 3

It is certified that error appears in the above-identified patent and that said Letters Patent is hereby corrected as shown below:

At Figure Sheet 5 of 5, please replace Fig. 5 with the attached corrected replacement figure.

At column 2, line 67, please delete the phrase "18 or 78 percent" and insert the phrase --12 or 52 percent --.

At column 27, please replace Table VIII with the following corrected replacement table:

TABLE VIII
A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR[b]Niacin | | | | | | | | |
| AST | 23.8 | 27.9 | 40.4 | 36.6 | 56.5 | na | 97.0 | |
| % | -- | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | -- | na | 98 | 113 | 109 | 114 | 114 | |
| McKenney SR Niacin | | | | | | | | |
| AST | 25.6 | 29.5 | 36.3 | 39.0 | 59.1 | na | 100.0 | |
| % | -- | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | -- | na | 87 | 106 | 100 | 105 | 102 | |
| McKenney SR Niacin | | | | | | | | |
| ALK | 95 | 95 | 106 | 105 | 136 | na | 135 | |
| % | -- | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | -- | na | 99 | 102 | 98 | 103 | 104 | |
| McKenney SR Niacin | | | | | | | | |
| Drop | -- | 0 | 1 | 2 | 4 | na | 5 | 12 |
| n | -- | -- | -- | -- | -- | -- | -- | 23 |
| % | -- | 0 | 4 | 9 | 17 | na | 22 | 52 |
| Invention Dosage | | | | | | | | |
| Drop | -- | -- | 0 | 0 | 0 | 0 | 0 | 0 |
| n | -- | -- | 26 | 67 | 97 | 35 | 15 | 240 |
| % | -- | -- | 0 | 0 | 0 | 0 | 0 | 0 |
| 1 year | -- | -- | 15 | 47 | 77 | 31 | 15 | 184 |
| 1 year | -- | -- | 58 | 69 | 79 | 89 | 100 | 77 |

Dosed twice-per-day as described in "A Comparison of the Efficacy and Toxic Effects of Sustained - vs. Immediate - Release Niacin in Hypercholesterolemic Patients" by McKenney et al., *Journal of the American Medical Association*, March 2, 1994; Vol. 271, No. 9, pages 672-677.
[b] SR is "sustained release"
[c] Dosed once-per-day at night

UNITED STATES PATENT AND TRADEMARK OFFICE
CERTIFICATE OF CORRECTION

PATENT NO. : 6,818,229 B1
APPLICATION NO. : 08/962027
DATED : November 16, 2004
INVENTOR(S) : Eugenio A. Cefali et al.

It is certified that error appears in the above-identified patent and that said Letters Patent is hereby corrected as shown below:

At column 27, line 46, please delete the phrase "had 18 of 23, or 78 percent" and insert the phrase --had 12 of 23, or 52 percent--.

Signed and Sealed this

First Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 6,818,229 B1  Page 1 of 1
APPLICATION NO. : 08/962027
DATED : November 16, 2004
INVENTOR(S) : Cefali et al.

It is certified that error appears in the above-identified patent and that said Letters Patent is hereby corrected as shown below:

On the Title page, under Item [63], Related U.S. Application Data, change "Continuation-in-part of application No. 08/814,974, filed on Mar. 6, 1997, now Pat. No. 6,129,930, which is a continuation-in-part of application No. 08/368,378, filed on Jan. 14, 1995, now Pat. No. 6,080,428, which is a continuation-in-part of application No. 08/124,392, filed on Sep. 20, 1993, now abandoned" to --Continuation-in-part of application No. 08/814,974, filed on Mar. 6, 1997, now Pat. No. 6,129,930, which is a continuation-in-part of application No. 08/368,378, filed on Jan. 4, 1995, now Pat. No. 6,080,428, which is a continuation-in-part of application No. 08/124,392, filed on Sep. 20, 1993, now abandoned--

Signed and Sealed this

Twenty-third Day of November, 2010

David J. Kappos
*Director of the United States Patent and Trademark Office*